United States Patent
Hawkins et al.

(10) Patent No.: US 9,248,026 B2
(45) Date of Patent: Feb. 2, 2016

(54) SURFACE EXPANDING SPACER

(71) Applicant: DePuy Synthes Products, Inc., Raynham, MA (US)

(72) Inventors: John Riley Hawkins, Cumberland, RI (US); Nicholas Pavento, North Attleboro, MA (US); Christopher Ramsay, West Wareham, MA (US); Sean Selover, Westport, MA (US); Kevin Lee, Canton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 184 days.

(21) Appl. No.: 13/797,174

(22) Filed: Mar. 12, 2013

(65) Prior Publication Data

US 2014/0058515 A1    Feb. 27, 2014

Related U.S. Application Data

(60) Provisional application No. 61/692,326, filed on Aug. 23, 2012.

(51) Int. Cl.
 *A61F 2/44* (2006.01)
 *A61F 2/46* (2006.01)
 *A61F 2/30* (2006.01)

(52) U.S. Cl.
 CPC ............. *A61F 2/4455* (2013.01); *A61F 2/4601* (2013.01); *A61F 2/4611* (2013.01); *A61F 2/4644* (2013.01); *A61F 2002/30523* (2013.01); *A61F 2002/30571* (2013.01); *A61F 2002/30579* (2013.01); *A61F 2002/30594* (2013.01); *A61F 2002/30772* (2013.01); *A61F 2002/4627* (2013.01); *A61F 2002/4629* (2013.01); *A61F 2002/4645* (2013.01)

(58) Field of Classification Search
 CPC .................................................... A61F 2/4455
 See application file for complete search history.

(56) References Cited

U.S. PATENT DOCUMENTS

| | | |
|---|---|---|
| 5,665,122 A | 9/1997 | Kambin |
| 6,039,761 A | 3/2000 | Lehmann |
| 6,193,757 B1 | 2/2001 | Foley |
| 6,723,126 B1 | 4/2004 | Berry |
| 7,585,316 B2 * | 9/2009 | Trieu ............................ 606/279 |
| 7,879,098 B1 | 2/2011 | Simmons |
| 2002/0007218 A1 | 1/2002 | Cauthen |
| 2004/0002760 A1 | 1/2004 | Boyd et al. |
| 2009/0099610 A1 | 4/2009 | Johnson et al. |
| 2012/0089231 A1 | 4/2012 | Prestigiacomo |

FOREIGN PATENT DOCUMENTS

WO    WO 2007078692    7/2007

OTHER PUBLICATIONS

Pederson, "Thermal assembly of a biomimetic mineral/collagen composite", *Biomaterials* 24: 4881-4890 (2003.

* cited by examiner

*Primary Examiner* — Andrew Yang

(57) ABSTRACT

An interbody spacer comprising a series of stacked walls connected by a common base, wherein the spacer collapses when pressed into an access delivery tube. During insertion, the walls can flex as a unit, like bending a deck of cards, to traverse bends in the access tube. Upon distally exiting the portal of the access delivery tube, the walls track apart (like spreading fingers) to create a wide base of support for the vertebral body endplate. A graft delivery device that uses a conveyor belt-type approach to deliver bone graft from the device to a location in a patient. In some embodiments, the conveyor-belt is manually actuated.

10 Claims, 39 Drawing Sheets

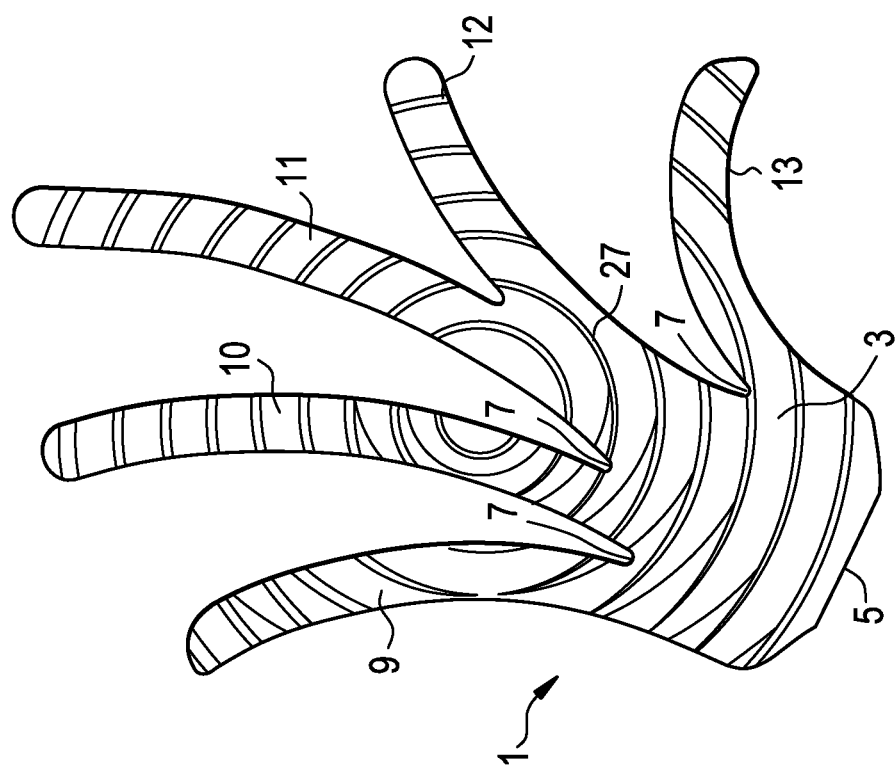

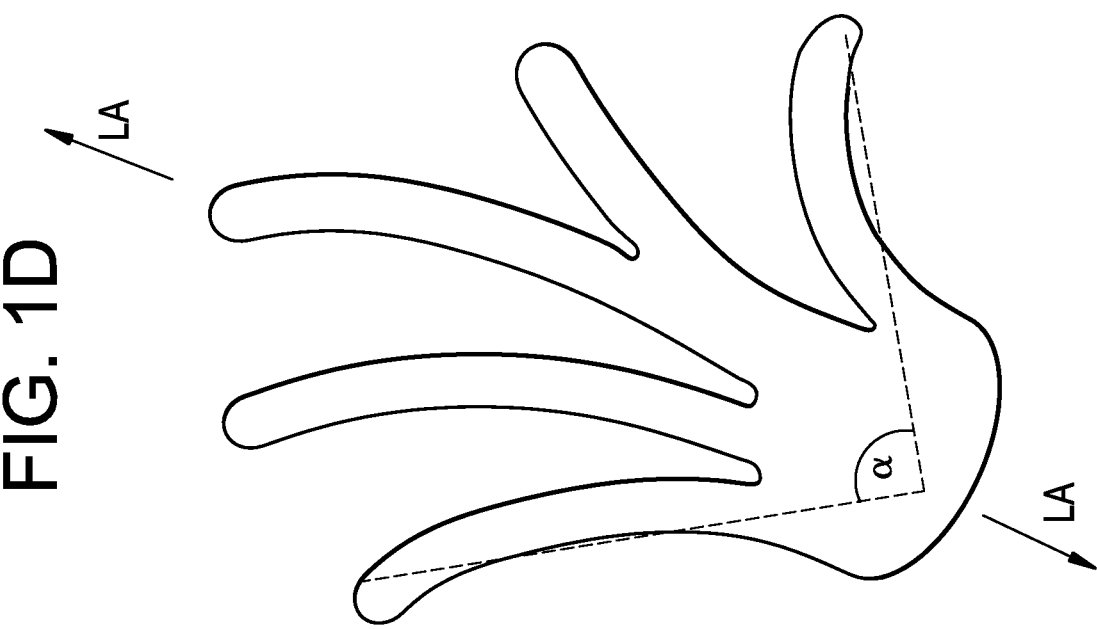

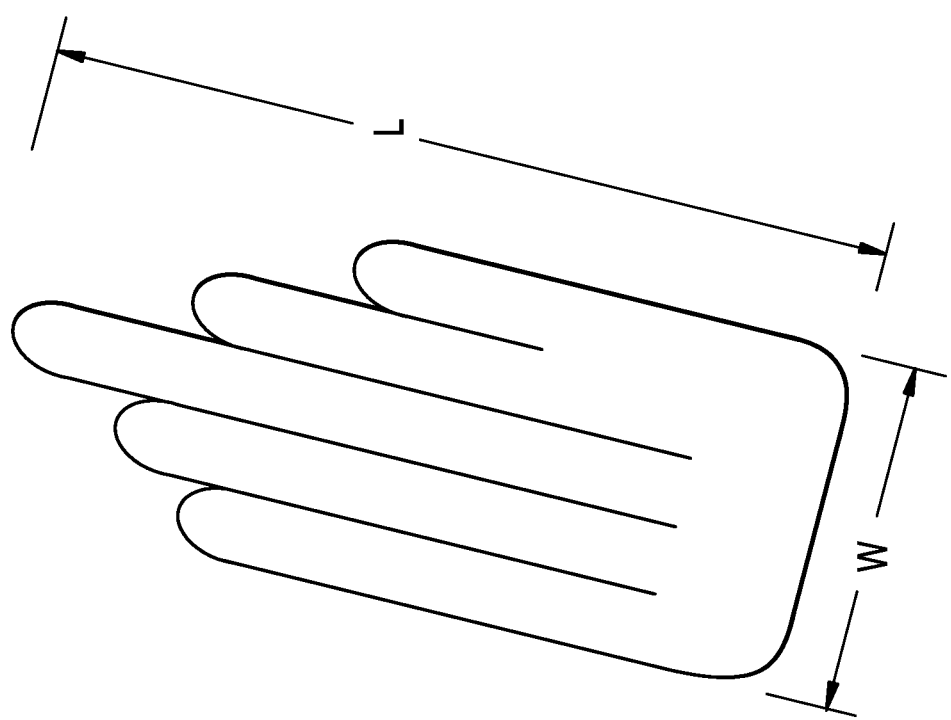

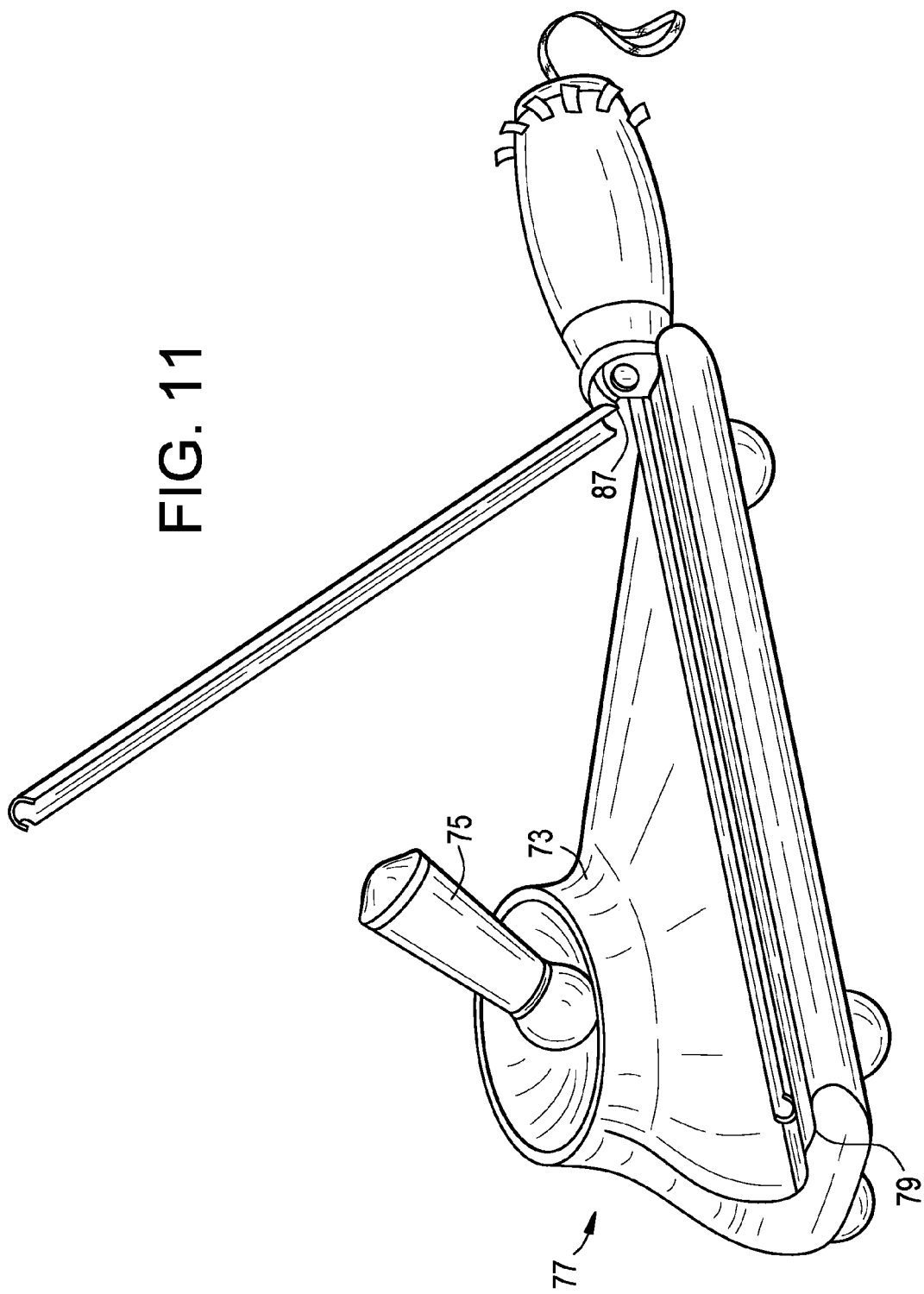

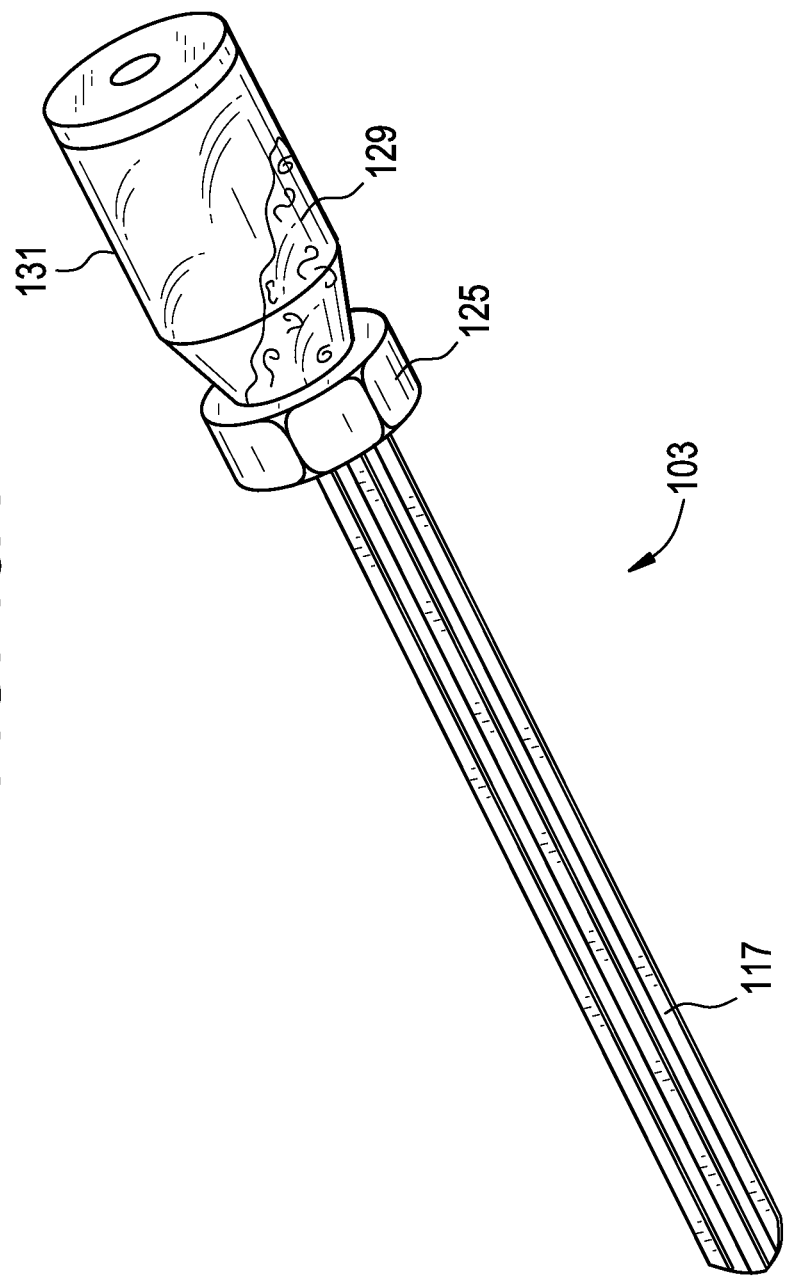

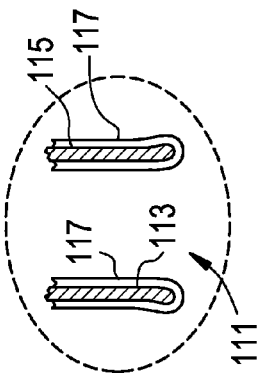
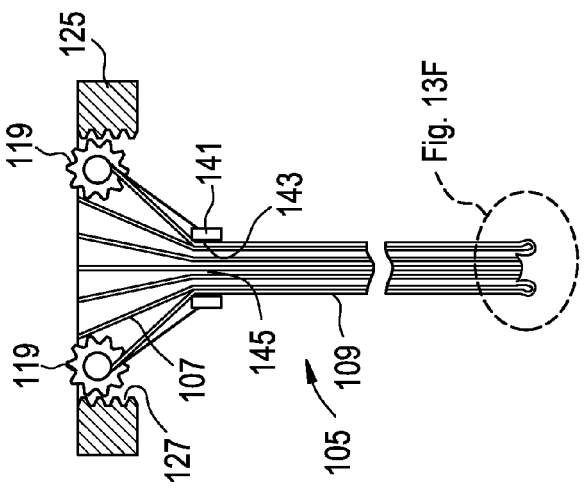
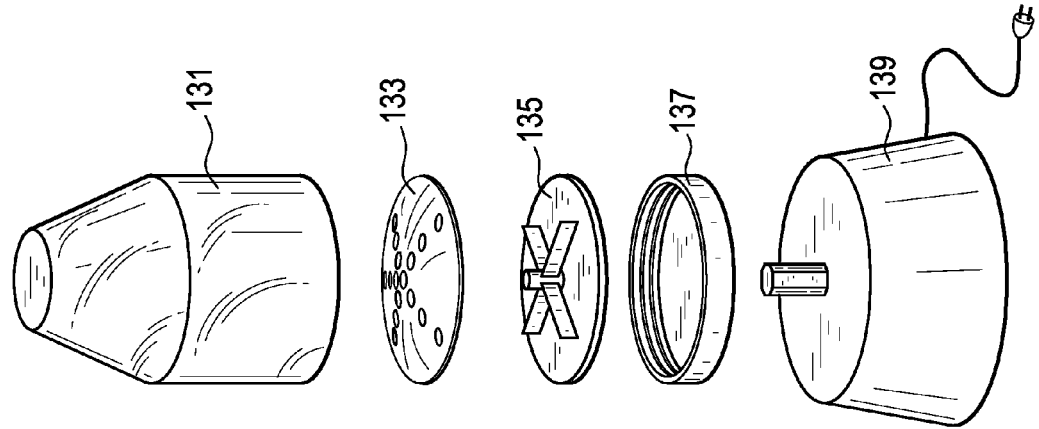

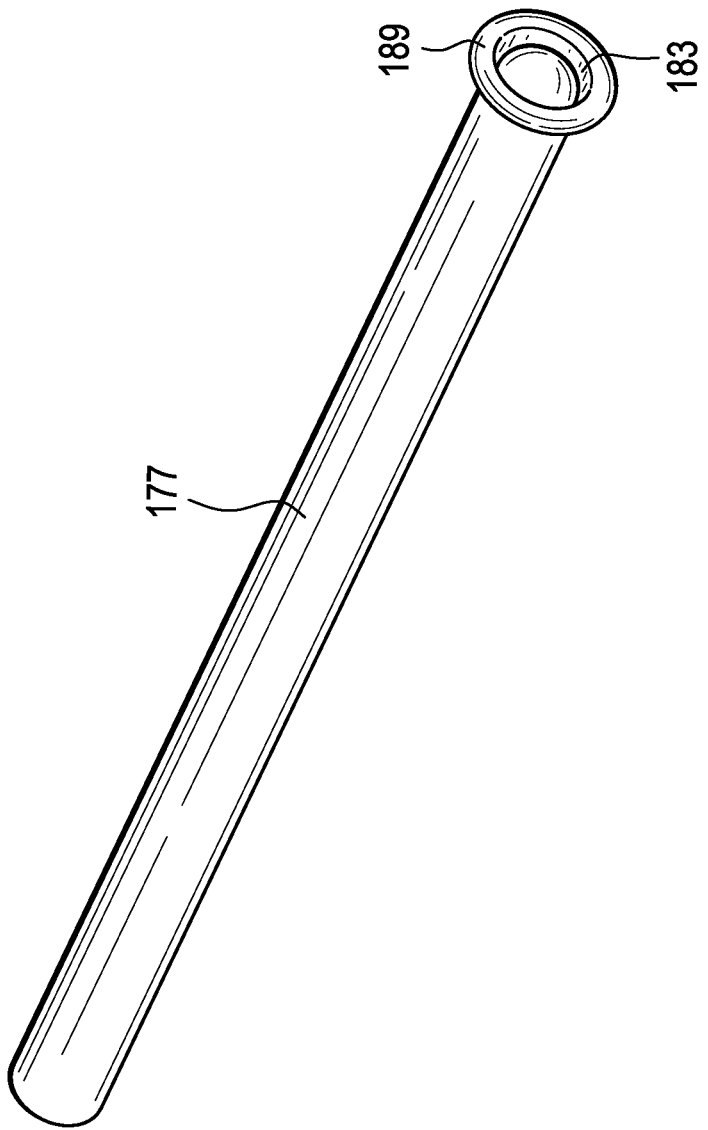

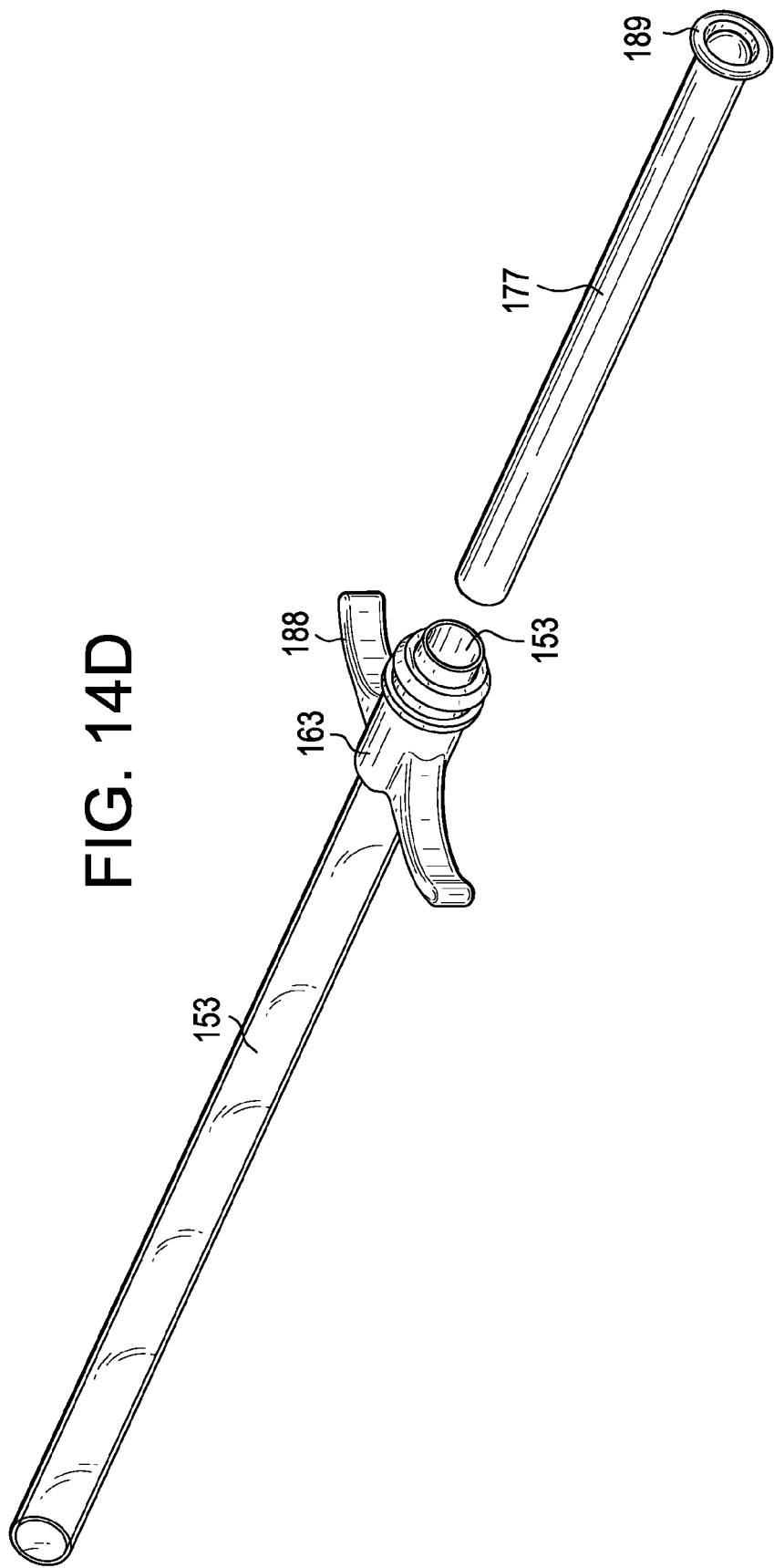

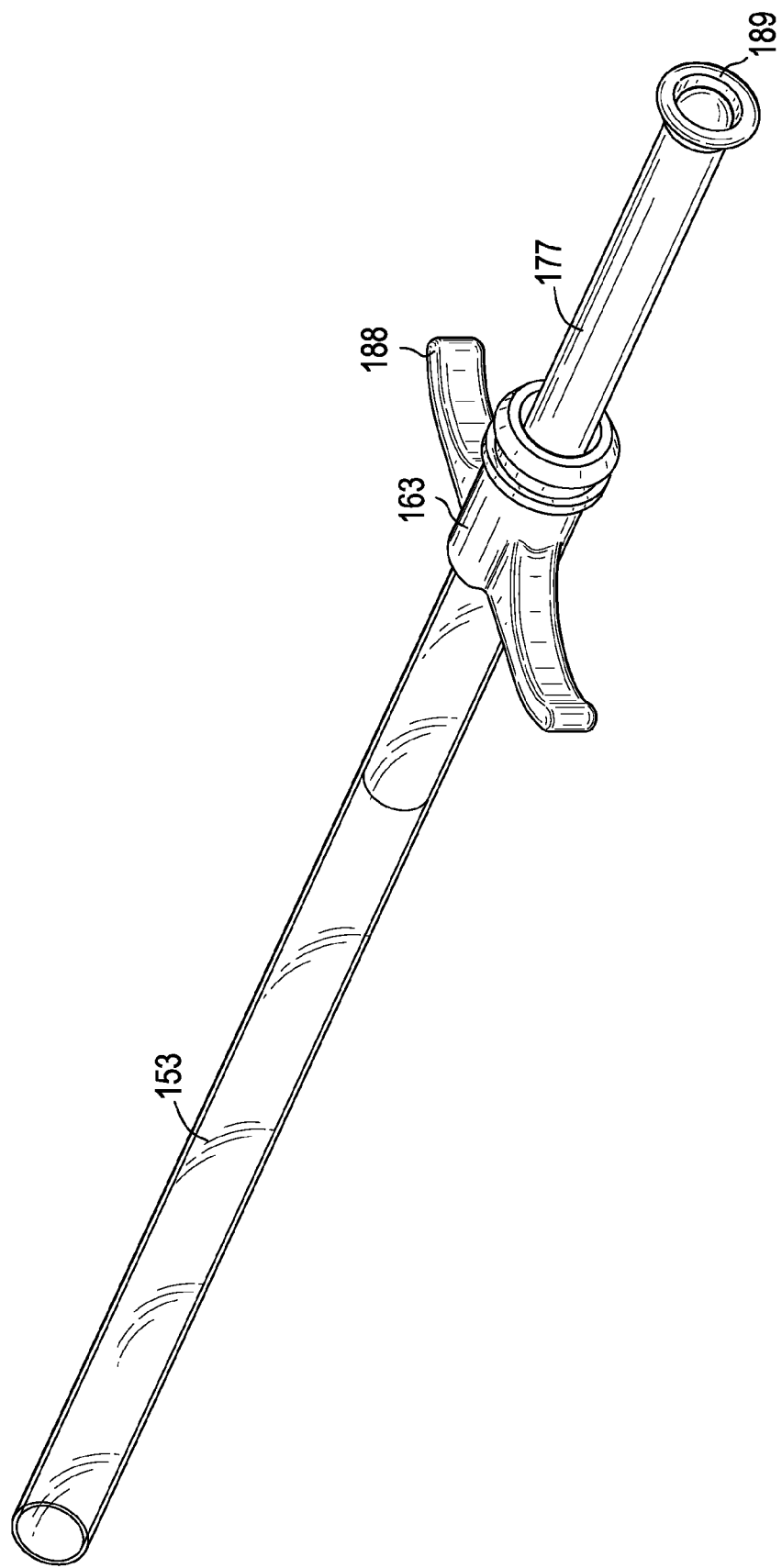
FIG. 14E1

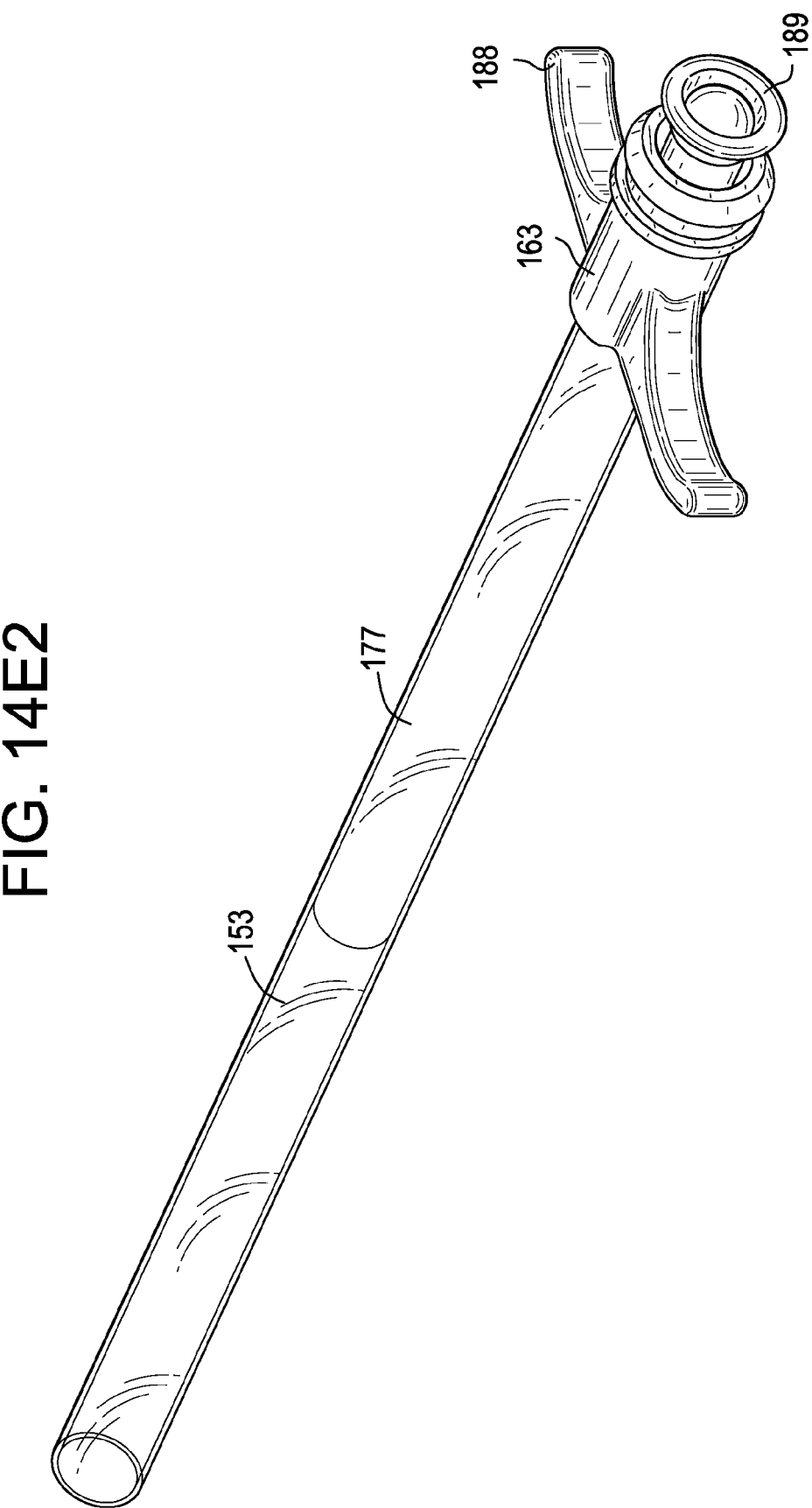
FIG. 14E2

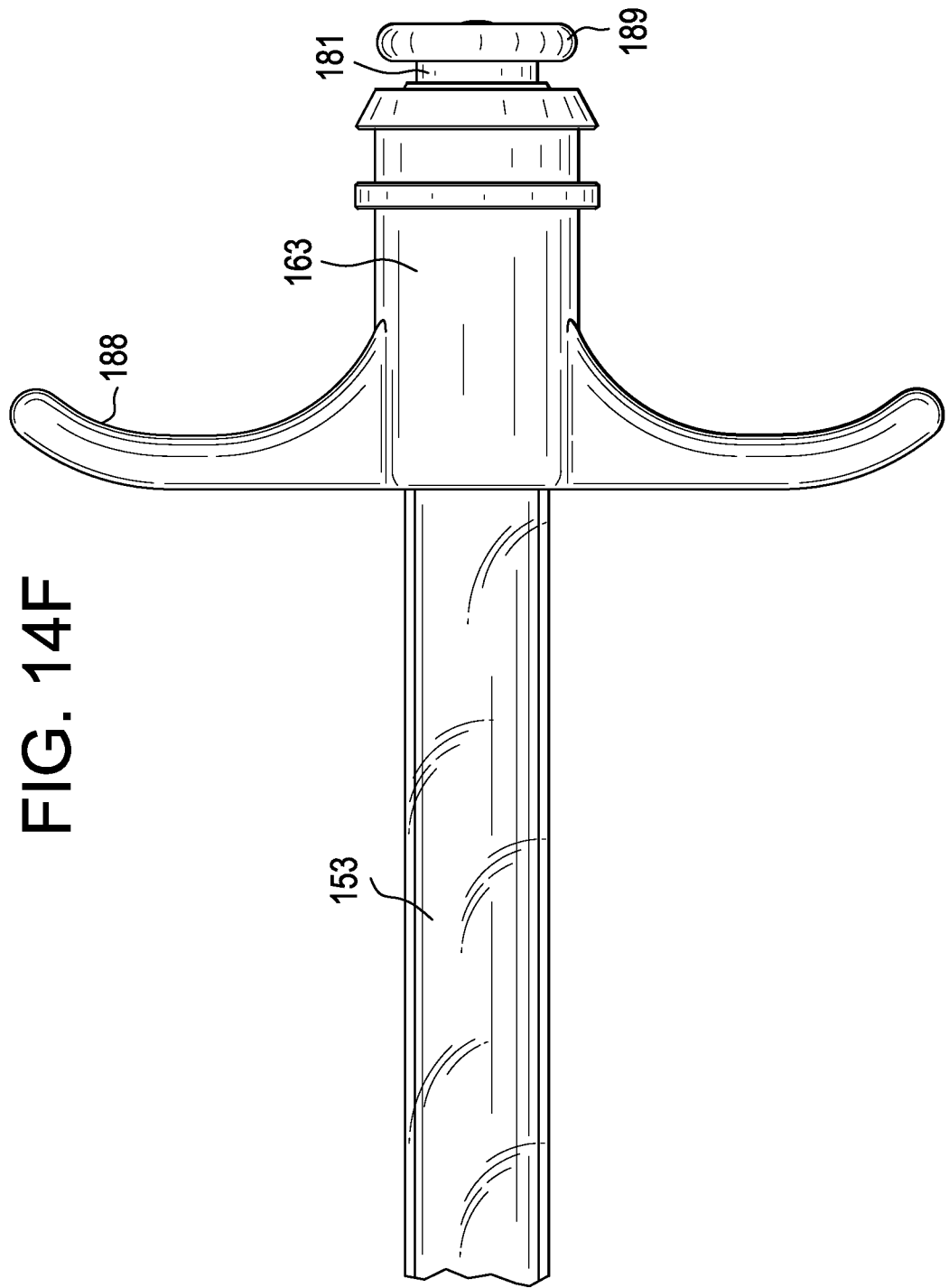

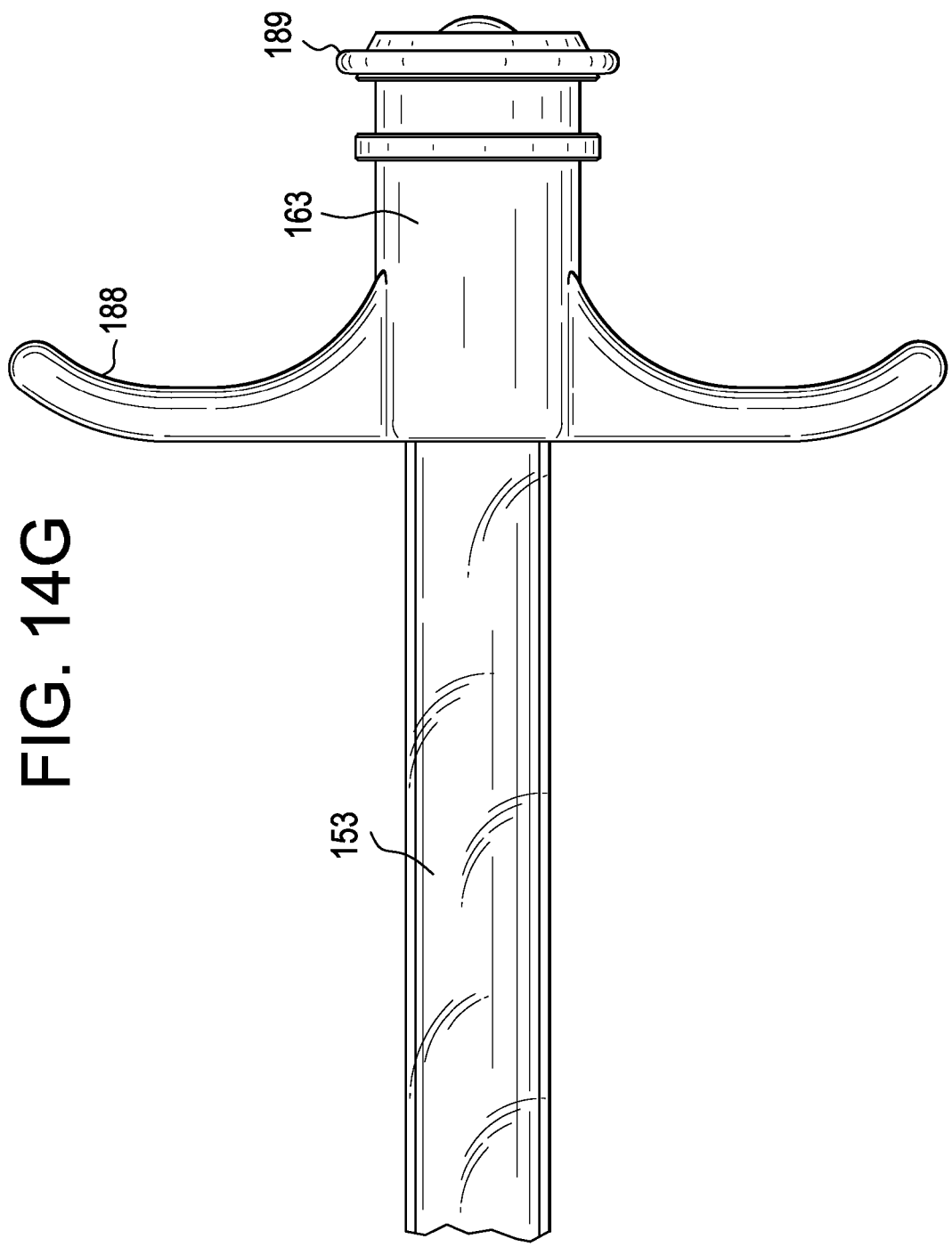

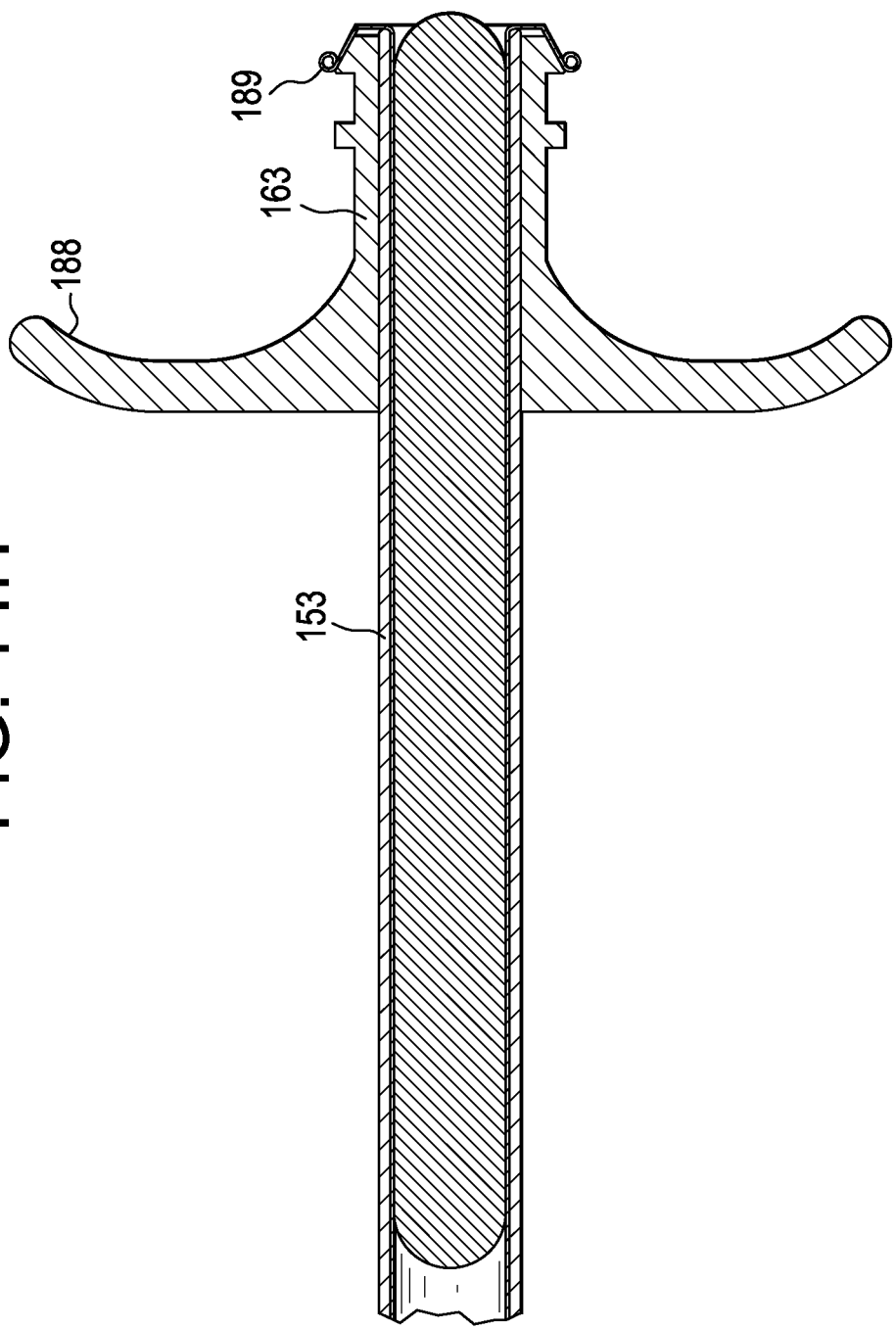

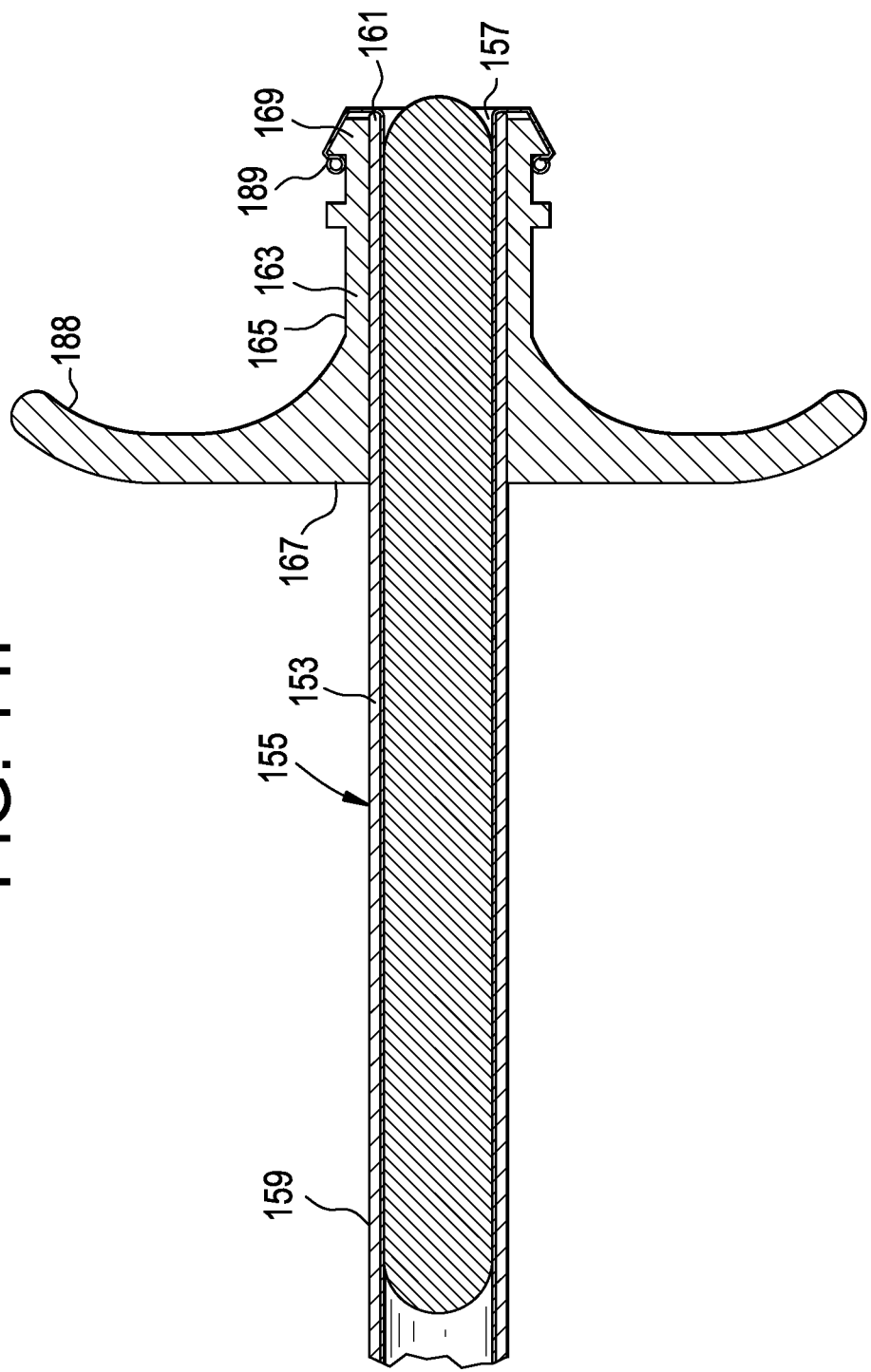

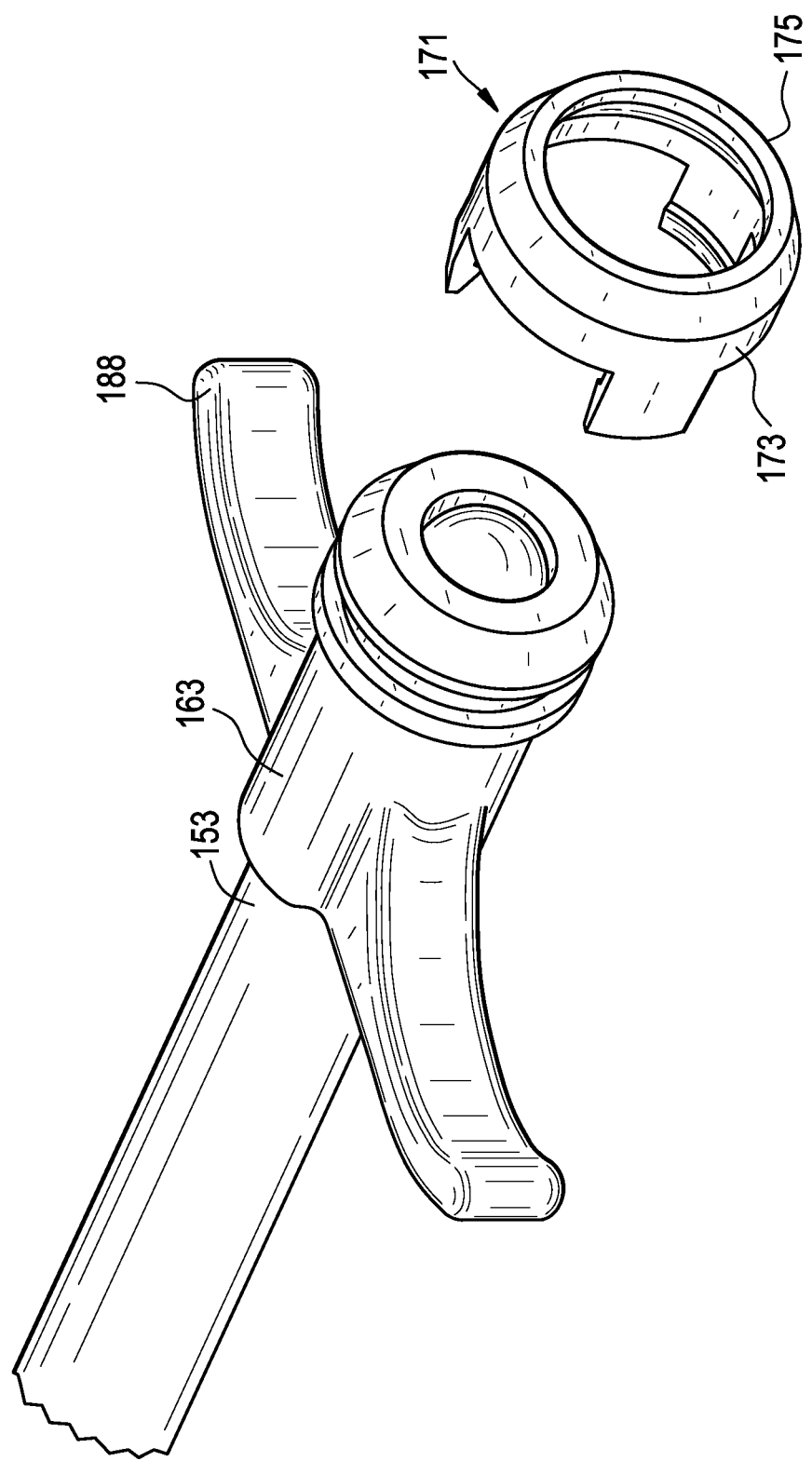

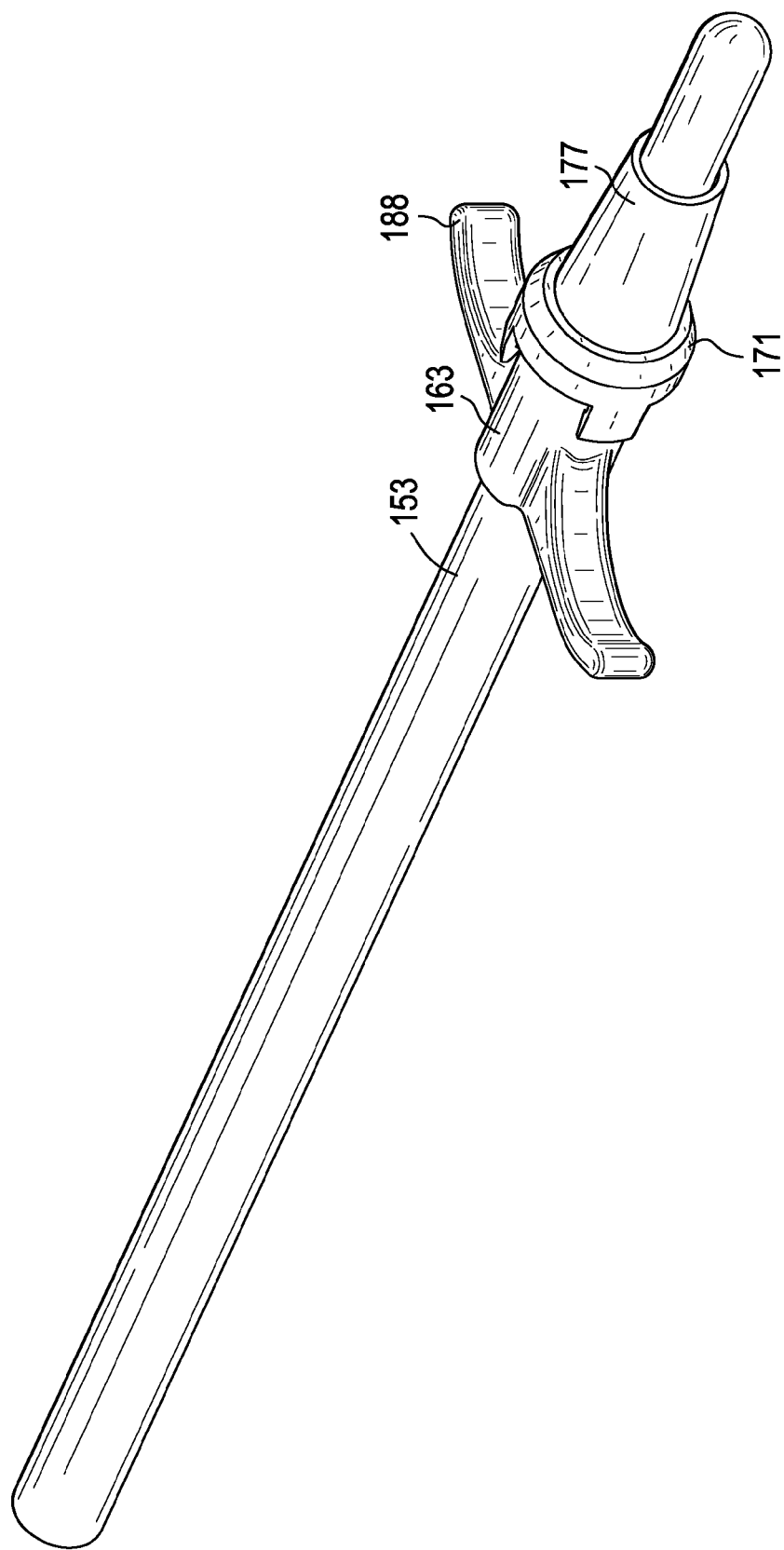

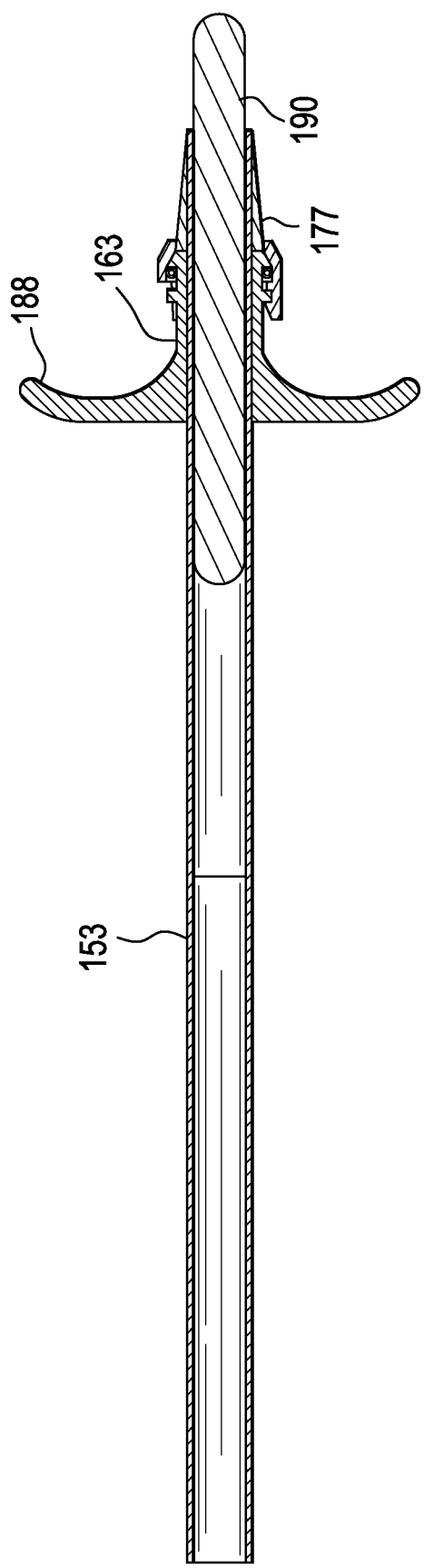

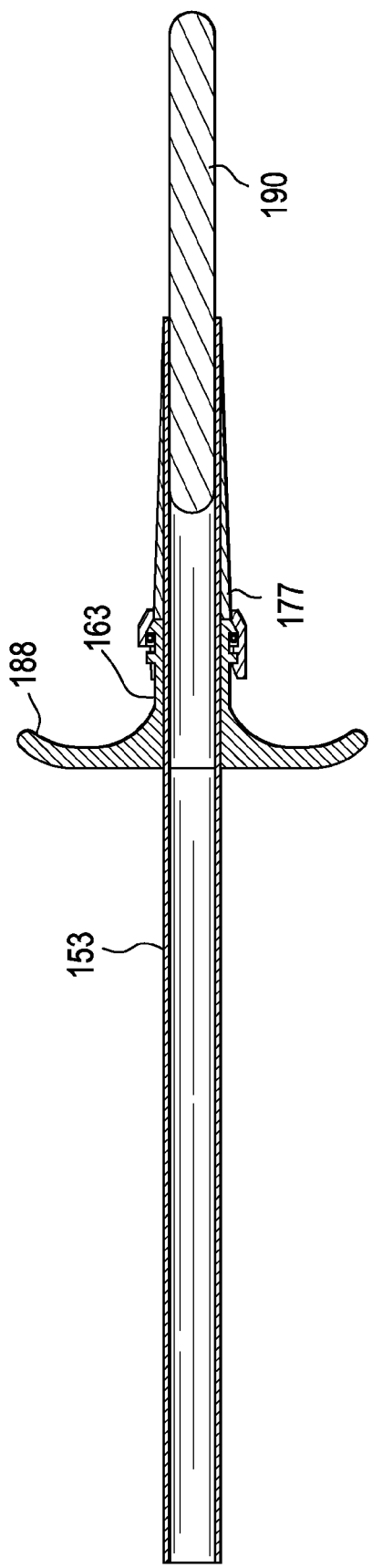

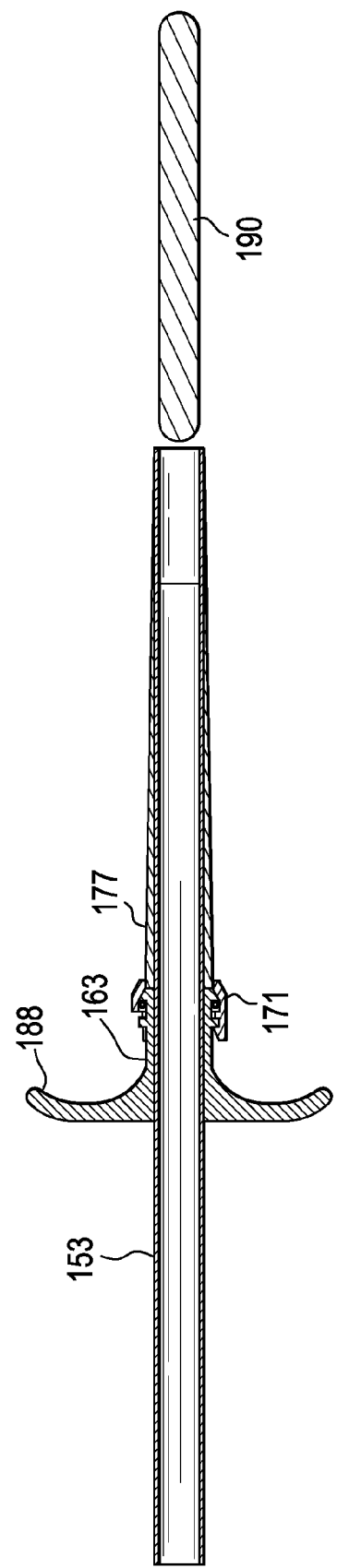

SURFACE EXPANDING SPACER

CONTINUING INFORMATION

This patent application claims priority from U.S. Provisional patent application U.S. Ser. No. 61/692,326, filed Aug. 23, 2012, entitled "Surface Expanding Spacer", (Hawkins et al.), the specification of which is incorporated by reference in its entirety.

BACKGROUND OF THE INVENTION

Although the use of intervertebral spacers is widespread in spine surgery, they present a notable challenge. On the one hand, maximizing the amount of surface area of the spacer would appear to better distribute their loads prevailed upon the adjacent vertebral body endplates. On the other hand, maximizing the amount of space preserved for blood and bone graft material would appear to improve the quality and rate of biologic bone growth for fusion and healing. Currently, a tradeoff has been realized in conventional spacers through minimizing the wall thickness of cages to allow for inserted or packed graft or bone growth factor materials. However, this tradeoff may not only predispose the cage to subsidence, it also leads to spacers that are very wide in relation to the available surgical access trajectories, thereby minimizing the margin of safety during their approach.

U.S. Pat. Nos. 5,665,122; 7,879,098 and 6,723,126 each discloses a different multi-piece, expandable fusion cage.

U.S. Pat. No. 6,193,757 discloses a unitary expandable fusion cage having a pair of flanges flexibly connected on one end and pointing towards each other at the other end.

US Published Patent Application 2004-0002760 discloses a flexible device having a pair of flanges flexibly connected on one end and made of bone.

US Published Patent Application 2012-0089231 discloses a unitary expandable fusion cage having a pair of flanges connected on one end and pointing towards each other at the other end.

US Published Patent Application 2009-0099610 and PCT Published Patent Application WO2007-078692 each discloses an expandable stent-like device.

US Published Patent Application US2002-0007218 discloses a Y-shaped device.

SUMMARY OF THE INVENTION

The present invention relates to an interbody spacer comprising a series of stacked walls or fingers connected by a common base, wherein the spacer collapses when pressed into an access delivery tube. During insertion, the fingers can flex as a unit (like bending a deck of cards) to traverse bends in the access tube. Upon distally exiting the portal of the access delivery tube, the fingers of the spacer spread apart (like spreading fingers) to create a wide base of support for the vertebral body endplate.

Therefore, in accordance with the present invention, there is provided a unitary intervertebral fusion cage comprising:
a) a base having a proximal surface and a distal surface, and
b) at least three elastically deformable fingers extending distally from the base in a plane.

Also in accordance with the present invention, there is provided a unitary intervertebral fusion cage comprising:
a) a proximal base and
b) a plurality of elastically deformable fingers extending from the base in a plane, wherein a first finger extends substantially distally, a second finger extends substantially anteriorly and a third finger extends substantially posteriorly.

Also in accordance with the present invention, there is provided a unitary intervertebral fusion cage comprising:
a) a base and
b) a plurality of elastically deformable fingers extending from the base in a plane,
c) wherein a first and second finger form an angle of at least 45 degrees.

Also in accordance with the present invention, there is provided a unitary intervertebral fusion cage comprising:
a) a base having a proximal surface and a distal surface, and
b) a plurality of elastically deformable fingers extending distally from the distal surface of the base in a plane, wherein each finger has a tip, wherein the tips correspond substantially to a perimeter of a vertebral endplate.

Also in accordance with the present invention, there is provided a unitary intervertebral fusion cage having a collapsed form and an expanded form, the cage comprising:
a) a proximal base and
b) a plurality of elastically deformable fingers extending from the base in a plane, wherein the cage in its collapsed form has a length of at least 45 mm and a length-to-width ratio of at least 2.5:1.

Also in accordance with the present invention, there is provided a unitary intervertebral fusion cage having a collapsed form and an expanded form, the cage comprising:
a) a base and
b) a plurality of elastically deformable fingers extending from the base in a plane, each finger having a tip,
wherein the expanded form has a longitudinal axis,
wherein the tips of first and second fingers extend laterally from the longitudinal axis.

Graft material can be injected around and through the fingers via windows in the fingers. Alternatively, and uniquely to this invention, graft can be injected into the disc space prior to cage insertion and the fingers' narrow distal profile allows for facile penetration into the graft by the cage. Annular fibers of the disk prevent graft expulsion.

DESCRIPTION OF THE FIGURES

FIGS. 1A-D disclose spacers of the present invention in their expanded condition.

FIG. 11 discloses a mixing unit used with the first delivery device of the present invention.

FIGS. 13A-F disclose a second delivery device of the present invention.

DETAILED DESCRIPTION OF THE INVENTION

Figure 1C:
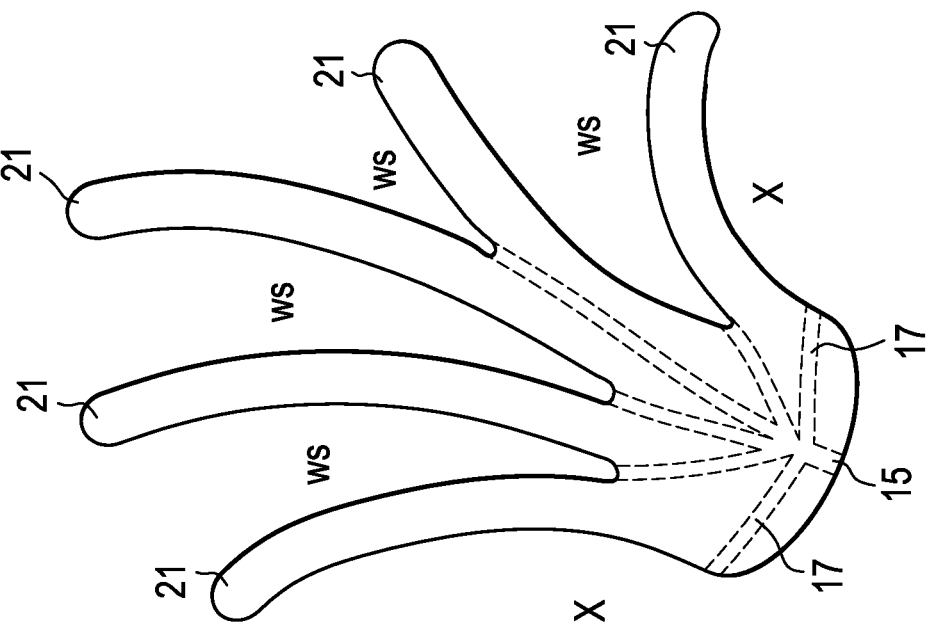

For the purposes of the present invention, the wall components of the spacer may also be referred to as "fingers". For the purposes of the present invention, an area between adjoining fingers may be referred to as "web space" or "WS".

Now referring to FIG. 1A, there is provided a unitary intervertebral fusion cage 1 comprising:
a) a base 3 having a proximal surface 5 and a distal surface 7, and
b) first, second, third, fourth and fifth elastically deformable fingers 9,10, 11,12, 13 extending distally from the base in a plane.

Figure 1B:
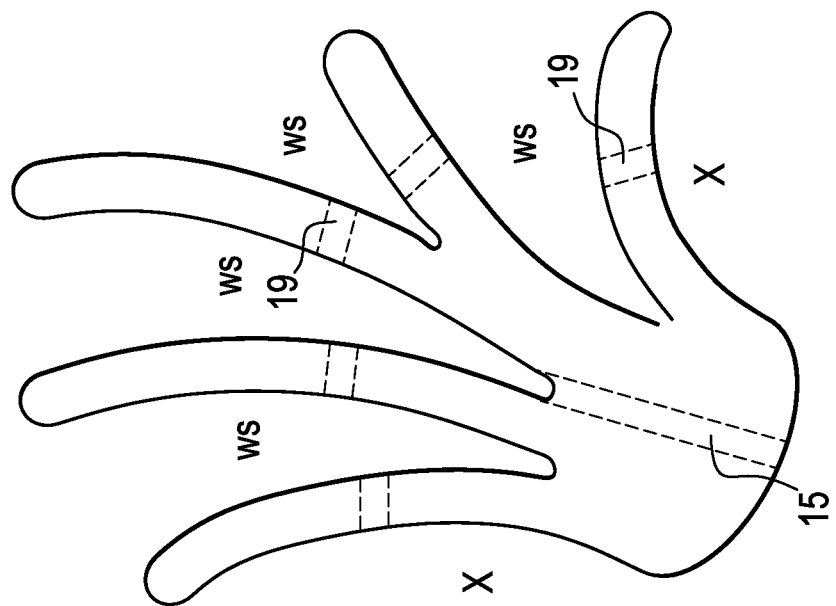

As shown in FIG. 1B, the cage may further comprise a throughhole 15 beginning on a proximal surface of the base and opening on a distal surface of the base. This throughhole allows cement to be injected into a web space WS of the cage from the proximal base of the cage.

Also as shown in FIG. 1B, the cage may further have at least one finger comprising a substantially transverse throughhole 19. This type of throughhole allows cement to move laterally within the cage (i.e., from web space to web space), or to move from a web space to regions outside the spacer (such regions denoted as X).

In some embodiments, each finger comprises a substantially transverse throughhole. This feature allows cement to move freely throughout the disc space.

As shown in FIG. 1C, in some embodiments, the cage further comprises a throughhole 15 beginning on a proximal surface of the base and branching within the base into a plurality of tubes 17, wherein each tube opens onto a distal surface of the base. This branching throughhole allows cement to be injected into each web space WS associated with the cage and to regions X outside the spacer from a single injection point on the proximal surface of the base.

Figure 6:
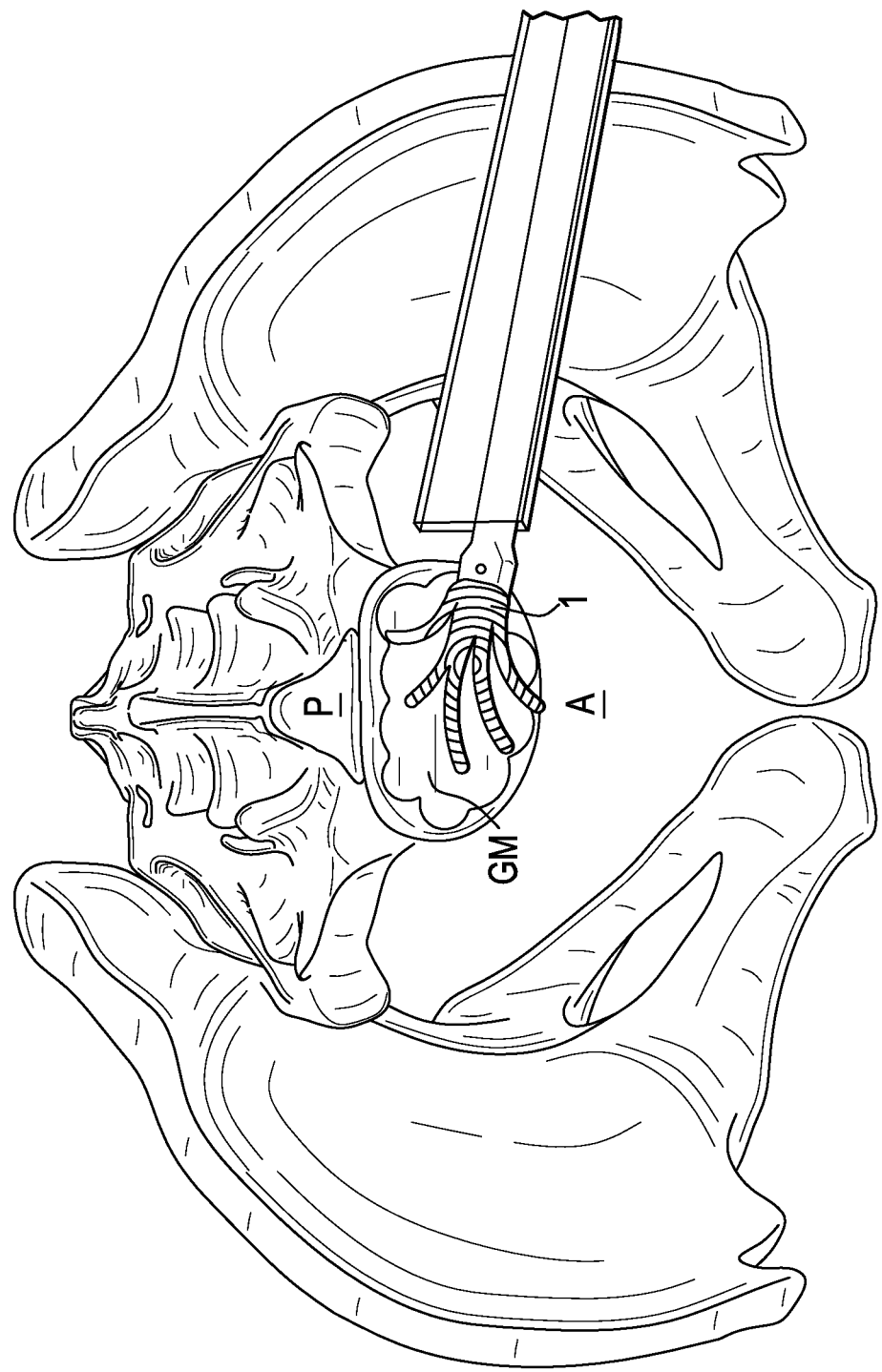
FIG. 6 shows the cage of the present invention in its fully expanded form within a graft-filled disc space.

In some embodiments, as shown in FIG. 1C, each finger has a tip 21, and the tips correspond substantially to a perimeter of a vertebral endplate. As shown in FIG. 6, this correspondence also provides for more balanced support of the vertebral endplates.

In some embodiments, as shown in FIG. 1D, the extreme fingers of the expanded cage form an angle α of at least 45 degrees. The angle α is obtained by drawing first and second lines connecting the midpoints of the beginning and end of each extreme finger (as shown in FIG. 1d), and measuring the angle produced by the intersection of these two lines. The greater divergence of the fingers of this embodiment (as compared to the prior art) provides for more balanced support of the vertebral endplates. Preferably, the extreme fingers form an angle of at least 60 degrees. More preferably, the extreme fingers form an angle of at least 90 degrees.

In some embodiments as shown in FIG. 1D, each finger has a tip 21 and the expanded form has a longitudinal axis LA. The tips of the extreme fingers may extend laterally from the longitudinal axis. This divergence of the tips from the longitudinal axis provides for more balanced support of the vertebral endplates.

The flexible nature of the fingers allow a curved spacer to transit a straight portal.

Also, an access portal positioned anterior of a desired location or oblique of a desired biomechanical trajectory can be used to deliver a cage that will steer towards or reside in the desired location. This provides a greater level of freedom and safety to the surgeon for avoiding soft tissue structures such as nerves, muscles and vessels.

Figure 8A:
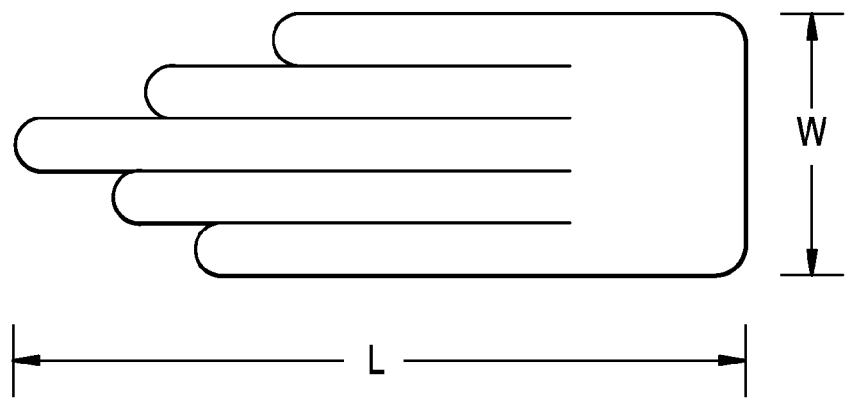
FIGS. 8A and 8b disclose top views of a cage of the present invention and a conventional intervertebral fusion cage.
Figure 8B:
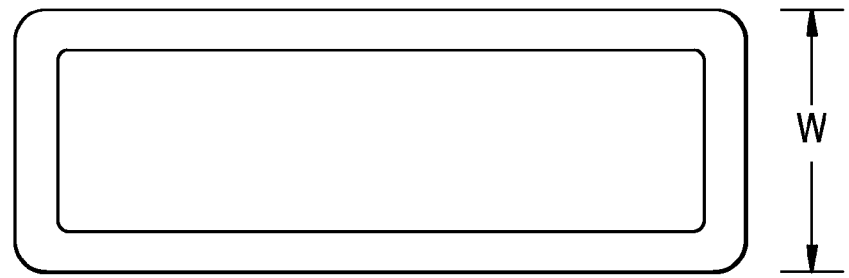

In general, the cages of the present invention provide a relatively large surface area for contacting against the vertebral endplates. By way of explanation, in the cages of FIGS. 8A and 8B, there is provided top views of a cage of the present invention in its closed condition and a conventional PLIF intervertebral fusion cage. Although each cage has an identical length L and widths W, the area of contact afforded by the upper surface of the cage of the present invention is more than 50% of the area represented by L×W. In contrast, the area of contact afforded by the conventional cage appears to be slightly less than 50% of the area represented by L×W. Preferably, the area of contact afforded by the upper surface of the cage of the present invention is more than 60% of the area represented by L×W, more preferably more than 70%, more preferably more than 80%. As well, although each cage has an identical length L and width W, the area of the vertebral endplate supported by the expanded present invention is more widely distributed. Preferably the distribution encompasses an additional 20% of the endplate surface area, more preferably an additional 33%, more preferably an additional 50%.

In some embodiments of the present invention, the surgeon first injects graft material into the disc space. This may be accomplished through a number or routes, including packing the bone graft into the disc space, and flowing a bone graft substance into the disc space. Once the graft material is in place, the surgeon then inserts the cage of the present invention into the disc space, with care being taken so that the fingers of the cage become extended before they meet the deposited bone graft. In this condition, the fingers enter the disc space by channeling through the bone graft material. This procedure also has the beneficial effect of enhancing the packing of the bone graft.

Now referring to FIGS. 2-6 there is provided a representation of the embodiment in which graft is first injected into the disc space followed by insertion of the cage of the present invention into the graft-filled disc space.

Figure 2:
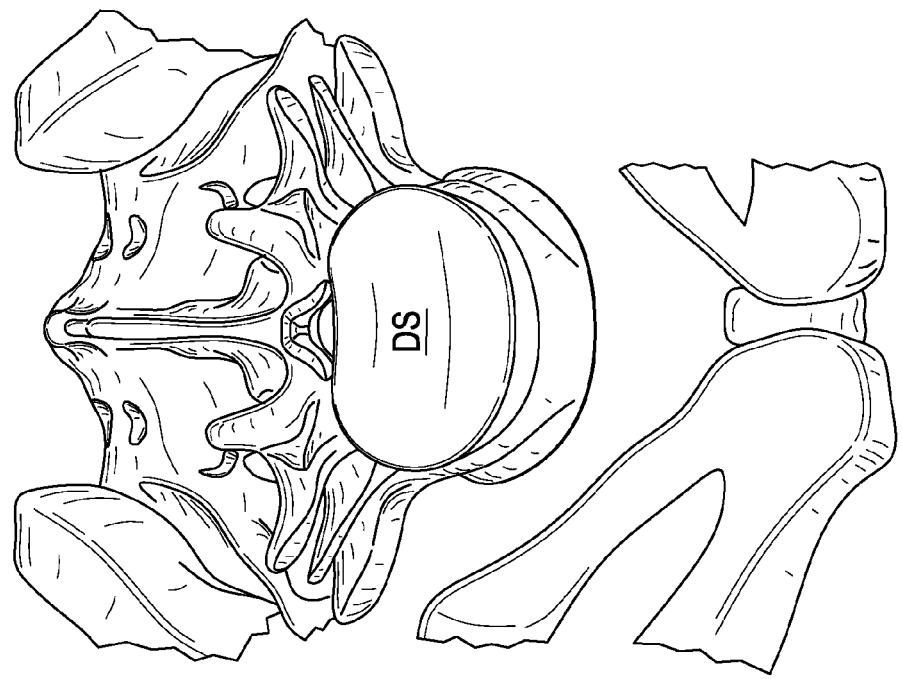
FIG. 2 shows a conventional lumbar disc space DS (with the upper vertebral body removed for purposes of clarity).

FIG. 2 shows a conventional lumbar disc space DS (with the upper vertebral body removed for purposes of clarity).

Figure 3:
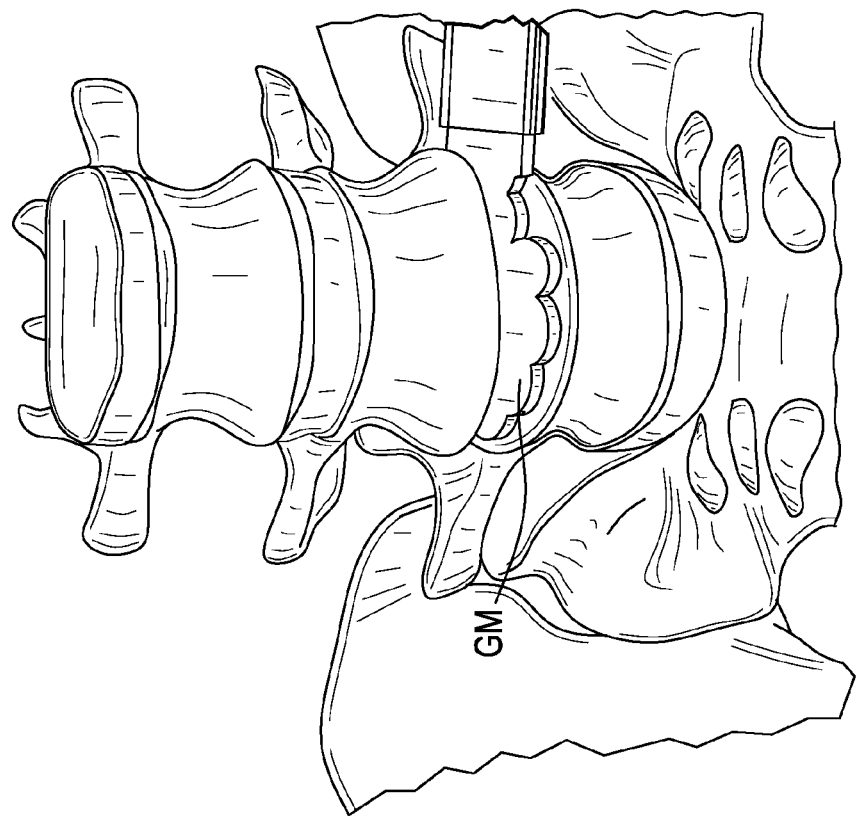
FIG. 3 discloses the injection of graft material GM into a conventional lumbar disc space FIG. 4A discloses a spacer of the present invention in its collapsed condition.

FIG. 3 discloses the injection of graft material GM into a conventional lumbar disc space In some embodiments, as shown in FIG. 4A, the cage has a collapsed form (as in FIG. 1E) and a expanded form (as in FIG. 1A), and the cage in its collapsed form has a length L of at least 45 mm and a length-to-width W ratio of at least 2.5:1. Such a cage is advantageously inserted via a lateral approach. The long length of the cage allows it to span across the conventional lumbar disc space, while its thin nature (as shown by its high aspect ratio) allows it to avoid nerves of the lumbar plexus located in the psoas during its lateral approach.

Figure 4B:
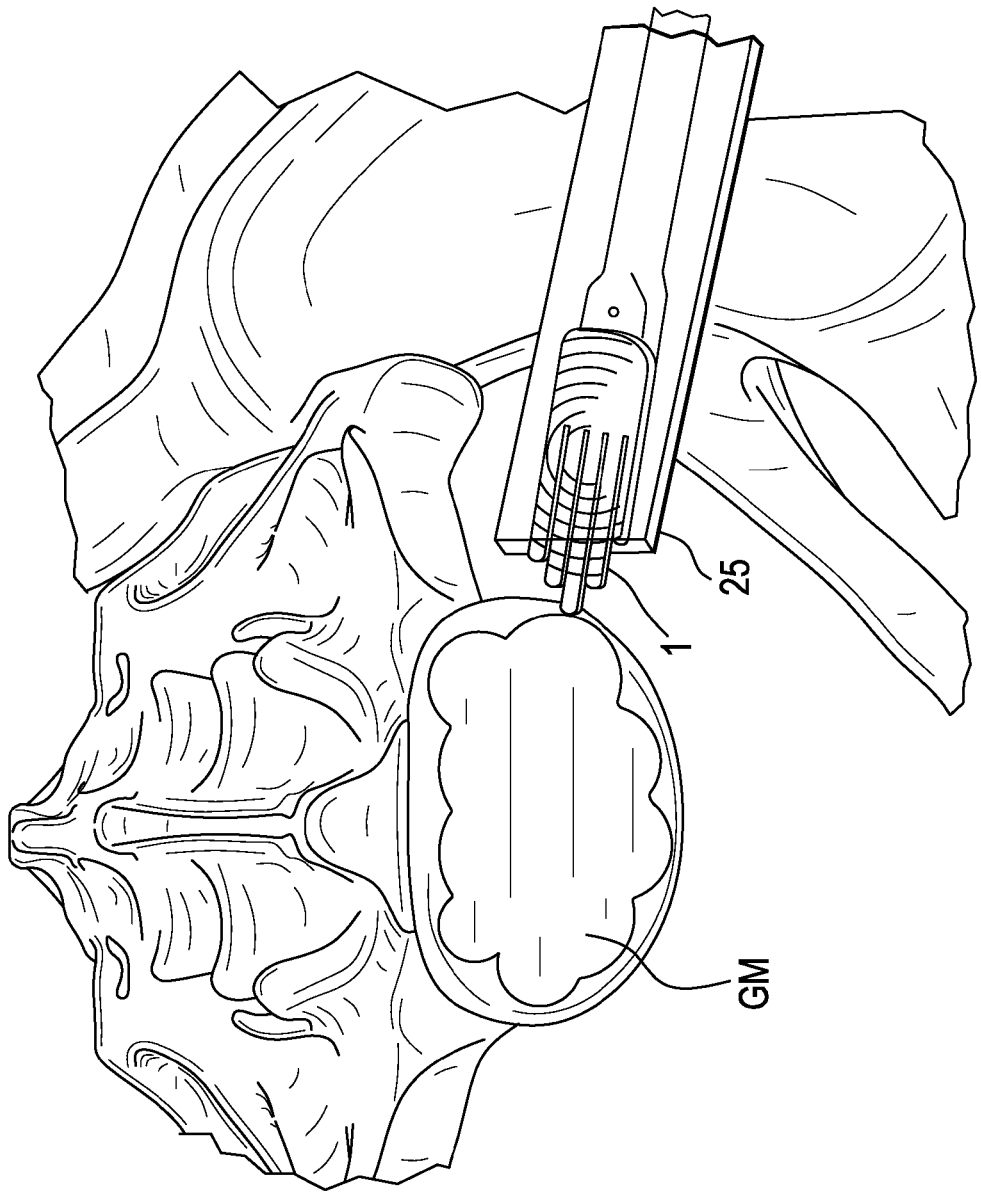
FIG. 4B shows the approach to the disc space of FIG. 3 of a cage of the present invention in its collapsed condition.

FIG. 4B shows the approach to the disc space of FIG. 4A of a cage of the present invention in its collapsed condition. The cage 1 is retained in its collapsed condition by its disposition within inserter 25. Inserter 25 comprises a hollow tube having a rectangular cross-section.

Figure 5:
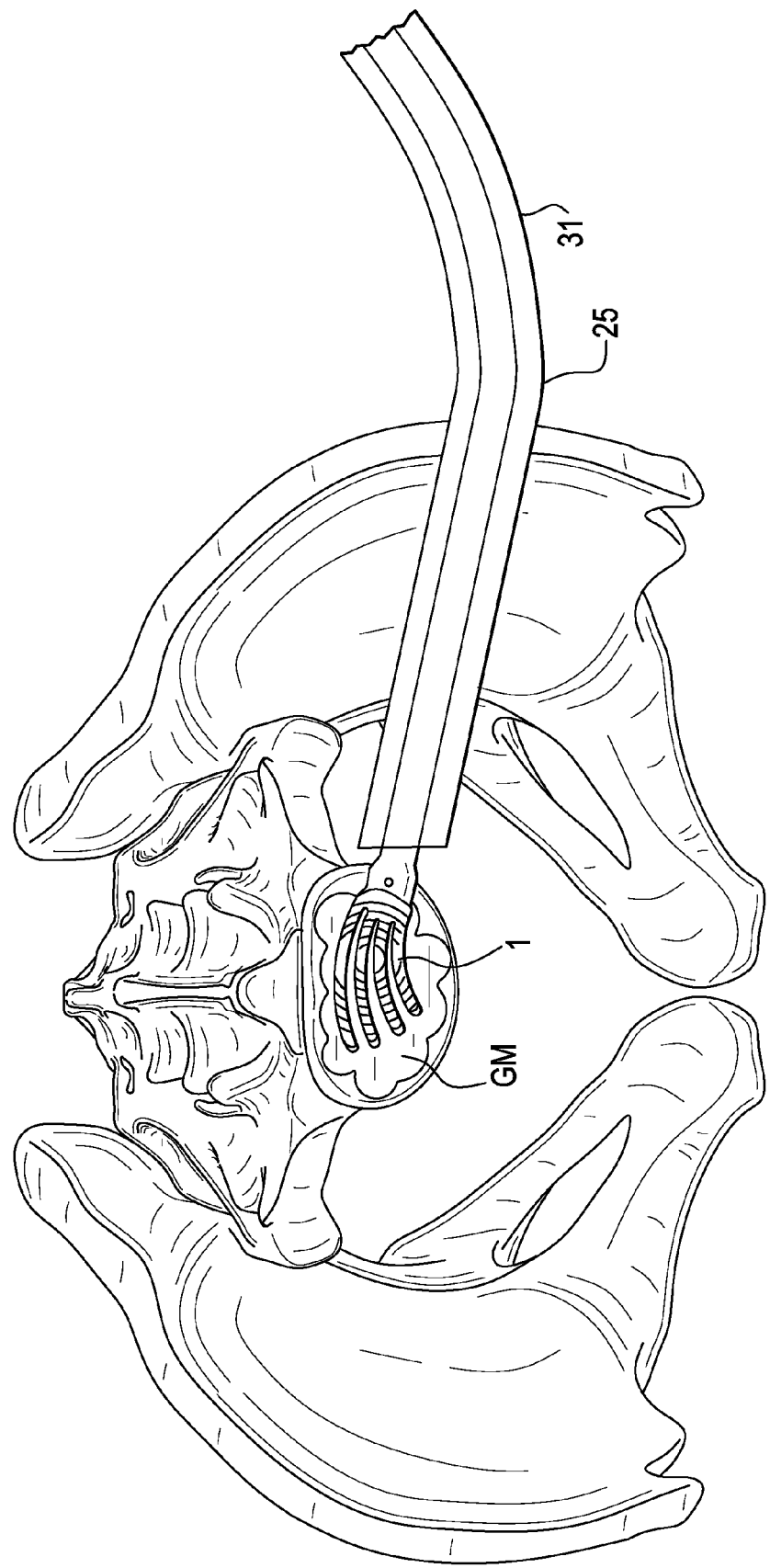
FIG. 5 shows the cage of the present invention in a partially expanded condition as it traverses the graft-filled disc space.

FIG. 5 shows the gradual expansion of the cage 1 of the present invention as it spans across the graft material-filled disc space.

FIG. 6 shows the cage 1 of the present invention in its fully expanded form within a graft-filled disc space.

Also as shown in FIG. 6, the cage may further have a first finger extending substantially distally, a second finger extending substantially anteriorly (A) and a third finger extending substantially posteriorly (P). The corresponding tips of these fingers correspond substantially to a perimeter of a vertebral endplate, thereby providing for substantially uniform coverage of the endplate.

In some embodiments (as in FIG. 1A), the cages of the present invention are provided with a throughhole extending distally from the proximal end of the cage. This throughhole opens distally onto one of the web spaces WS between the fingers, thereby allowing flowable bone graft to be injected into the disc space after cage placement. In some embodiments, throughholes are also provided transversely across at least one (and preferably all) of the fingers, thereby allowing the flowable bone graft to move between the different web spaces between the fingers from a central location.

One feature of the cage of the present invention is that its collapsed condition can be made more thin than a conventional static lateral cage while its expanded condition can be made of substantially equal width with conventional static lateral cages. However, as shown in FIG. 1A, the proximal end of the cage even in its expanded condition may still be relatively narrow. This narrow feature may allow the surgeon to first place and expand the cage, and then inject bone graft material not only into the central throughhole but also directly into the spaces lateral of the expanded cage (without proceeding through the central throughhole). Such lateral spaces are designated by an "X" in FIGS. 1B and 1C. The lateral placement of bone graft afforded by this embodiment allows greater uniformity of bone graft in the disc space.

Another feature of the cage of the present invention is that its uniformly slotted nature provides a degree of flexibility to the cage in its collapsed condition. This flexibility allows the cage to be laterally bent (similarly to the bending of a deck of cards). This ability to laterally bend can be exploited through advancing the collapsed cage through a non-linear cannula during its approach to the disc space. In some embodiments, the non-linear cannula that has a curved portion (preferably a curved distal end portion).

Therefore, in accordance with the present invention, there is provided an assembly comprising:
a) an inserter comprising a non-linear cannula,
b) a unitary intervertebral fusion cage comprising:
  i) a base having a proximal surface and a distal surface, and
  ii) at least two elastically deformable fingers extending distally from the base in a plane,
wherein the cage is disposed within the cannula.

In some embodiments (as in FIG. 1A), the cage of the present invention has teeth 27 extending from its upper and lower surfaces.

The intervertebral fusion cage of the present invention may be manufactured from any biocompatible flexible material suitable for use in interbody fusion procedures. In some embodiments, the cage comprises a composite comprising 40-99% polyarylethyl ketone PAEK, and optionally 1-60% carbon fiber. Such a cage is radiolucent. Preferably, the polyarylethyl ketone PAEK is selected from the group consisting of polyetherether ketone PEEK, polyether ketone ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. In some embodiments, the composite consists essentially of PAEK and carbon fiber. In some embodiments, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Spine, Raynham, Mass., USA. In some embodiments, the composite is PEEK-OPTIMA™, available from Invibio of Greenville, N.C.

In other embodiments, the cage is made from a flexible metal such as a titanium alloy such as nitinol.

In preferred embodiments, the cage is provided in a sterile form.

Typically, the inserter of the present invention can be made out of any material commonly used in medical instruments. If the inserter is designed to be reusable, then it is preferred that all of its components be made of stainless steel. If the device is designed to be disposable, then it is preferred that at least some of the components be made of plastic. Preferably, at least one component of the inserter is sterilized. More preferably, each component is sterilized.

Preferably, the inserter comprises a cannula having a substantially rectangular axial cross-section.

In some embodiments, the inserter comprises a non-linear cannula. Preferably, the non-linear cannula has a curved portion 31 (as in FIG. 5). Preferably, the non-linear cannula has a curved distal end portion.

Figure 7:
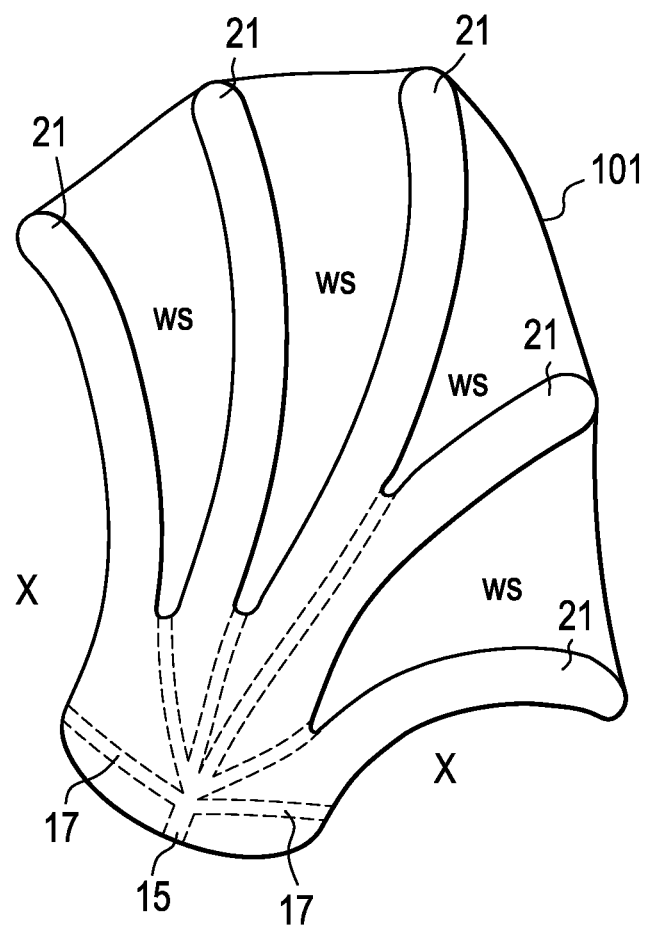
FIG. 7 discloses a cage of the present invention having a container enclosing the web spaces about its fingers.

In FIG. 7 discloses a cage of the present invention having a flexible container material 101 that connects the finger tips of the cage, thereby enclosing the web spaces about its fingers. In use, the container expands as the fingers expand. The cage of FIG. 7 is preferably used with an injectable type of graft material to be used after the cage is placed. When graft material is injected into the cage of FIG. 7, the container helps container the graft material within the web spaces. Because the container provides a containment function, the surgeon may inject large amounts of graft material into the web spaces, with the result being that the injected graft material becomes desirable packed into the web spaces.

In some embodiments, this container can be an inflatable material, while in others, the container can be a microporous material that retains the graft in the web spaces but allows for bone growth therethrough. In some embodiments, this container can be a ribbon of material that simply connects the finger tips, while in others, the container can be a bag that fully encloses the fingers in three dimensions.

Figure 9:
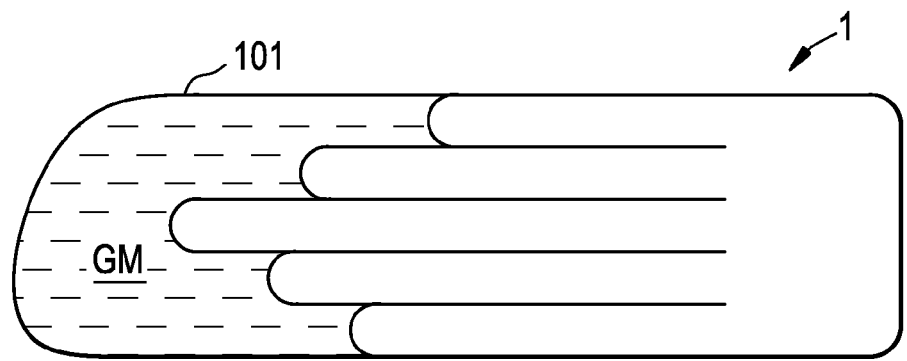
FIG. 9 discloses a top view of a cage-graft combination of the present invention.

In another embodiment, and now referring to FIG. 9, there is provided another embodiment preferably used with a non-injectable graft material type. The graft material GM would be placed between the container 101 (bag, ribbon of semi-flexible material, elastomeric band, etc) and the collapsed cage 1, adjacent to the distal face of the cage, prior to inserting the cage. As the cage exits the insertion cannula and expands, the container is tensioned, either by external attachments or by its attachment to the cage. This tension causes the graft material to be forced proximally between the fingers of the cage as they expand. Depending on its material and attachment, the container can then be either removed or left in place along with the cage.

In some embodiments, the material of construction for the fingers is a substantially homogenously porous material. The porosity is such that the graft material injected into the cage can flow through the porosity of the fingers, thereby providing for a substantially even distribution of the graft material between and outside the fingers of the cage.

Although the preferred approach for the cage of the present invention is a lateral approach, it is further contemplated that this cage may be inserted into the disc space from ALIF, TLIF and PLIF approaches as well. In each case, the cage provides a benefit of having a reduced width (during insertion) and a wide handprint (upon expansion).

In some embodiments, the graft material may be HEALOS FX, a flowable collagen-based material available from DePuy Spine of Raynham, Mass., USA.

In some embodiments, the graft material may comprises a bone forming agent.

In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including HBGF-1 and HBGF-2; growth differentiation factors (GDFs), members of the hedgehog family of proteins, including indian, sonic and desert hedgehog; ADMP-1; bone-forming members of the interleukin (IL) family; rhGDF-5; and members of the colony-stimulating factor (CSF) family, including CSF-1, G-CSF, and GM-CSF; and isoforms thereof.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are administered into the target disc space. In some embodiments, between about 1 microgram (µg) and about 1 mg of BMP are administered into the target disc space.

In many preferred embodiments, the bone forming agent is a porous matrix, and is preferably injectable.

The porous matrix of the present invention may contain porous or semi-porous collagen, extracellular matrices, metals (such as Ti, Ti64, CoCr, and stainless steel), polymers (such as PEEK, polyethylene, polypropylene, and PET) resorbable polymers (such as PLA, PDA, PEO, PEG, PVA, and capralactides), bone substitutes (such as TCP, HA, and CaP), autograft, allograft, xenograft, and/or blends thereof. Matrices may be orientated to enable flow from bony attachment locations to the aspiration port. Matrices may be layered with varying densities, pore structures, materials to enable increase stem filter at desired locations via density, pore size, affinity, as well as fluid flow control (laminar, turbilant, and/or tortuous path).

In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 µm, for example, between about 50 and about 250 µm. In yet other embodiments of the present invention, in situ porosity is produced in the injected matrix to produce a porous scaffold in the interbody space. Once the in situ porosity is produced in the space, the surgeon can inject other therapeutic compounds into the porosity, thereby treating the surrounding tissues and enhancing the remodeling process of the target tissue.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the interbody space.

In another embodiment, the treatment is delivered via injectable absorbable or non-absorbable cement to the target space. The treatment is formulated using bioabsorbable macro-sphere technologies, such that it will allow the release of the bone forming agent. The cement will provide the initial stability required to treat pain in target tissues. These tissues include, but are not limited to, hips, knee, vertebral body and iliac crest. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
  a) a first formulation comprising an acid-soluble type I collagen solution (preferably between about 1 mg/ml and about 7 mg/ml collagen) and
  b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Specific matrices may be incorporated into the device to provide load bearing qualities, enable directional bone formation, and/or control density of regenerated bone (cortical vs cancellous) or enable cell formation for soft tissue attachment. Nanotubes or nanocrystals can be orientated in a generally axial direction to provide for load bearing abilities as well as capillary wicking of vascular flow to further enhance directional bone formation. Biocompatible nanotubes can currently be produced from either carbon or titanium or bone substitutes including Ca, HA, and TCP.

In one embodiment, the bone forming agent is a plurality of viable ex vivo osteoprogenitor cells. Such viable cells, introduced into the interbody space, have the capability of at least partially supplementing the in situ drawn stem cells in the generation of new bone for the interbody space.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable ex vivo cells are selected as an additional therapeutic agent or substance, the viable cells comprise mesenchymal stem cells (MSCs). MSCs provide a special advantage for administration into the interbody space because it is believed that they can more readily survive the relatively harsh environment present in the space; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the interbody space are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the interbody space.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

A matrix may be made from hydrogels or may incorporate a hydrogel as component of the final structure. A hydrogel may be used to expand and enhance filling, improve handling characteristics or increase vacuum pressure. The increased vacuum pressure may be used to determine adequate hydration/stem cell filtration.

In all cases, excess bone marrow aspirate can be collected and mixed with added graft extenders including collagen like the HEALOS™, and HEALOS FX™, each of which is available from DePuy Spine Inc, Raynham, Mass., USA.

Although the present invention has been described with reference to its preferred embodiments, those skillful in the art will recognize changes that may be made in form and structure which do not depart from the spirit of the invention.

It was observed by the present inventors that pumping graft into the disc space through the implant of the present invention was somewhat difficult. In particular, it was found that pumping graft out of a delivery device was challenging. Moving granulated bone graft in a small tube, funnel or syringe with a plunger requires significant force.

That force can undesirably separate the liquid component (e.g., bone marrow aspirate) of the bone graft from the solid component. Over-compression of the bone graft could also alter the fusion environment. To that end, a number of inventions have been developed that overcome these difficulties. These inventions are based upon using a conveyor belt to transport the graft from the device to the disc space without changing the packing density of the graft.

Figure 10:
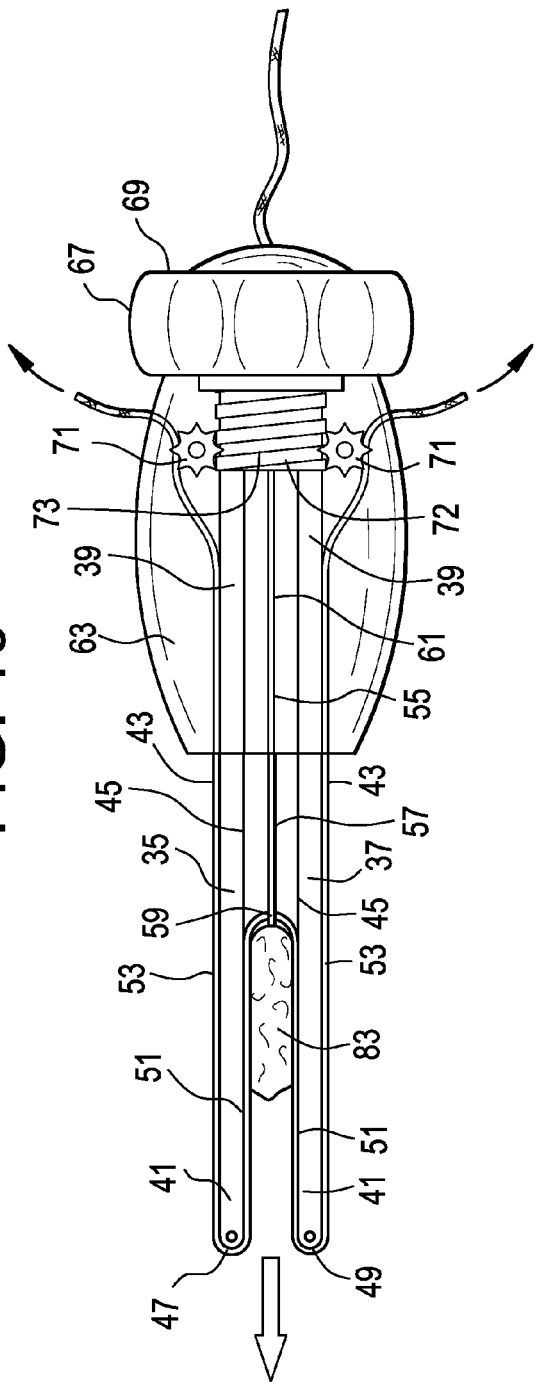
FIG. 10 discloses a cross-section of the first delivery device of the present invention.

In a first delivery device embodiment, and now referring to FIG. 10, there is provided a delivery device 33 for delivery graft, comprising;
  a) upper 35 and lower 37 opposing arms, each arm having a proximal end portion 39 and a distal end 41, an outer surface 43 and an inner surface 45,
  b) upper 47 and lower 49 ribbons, each ribbon having an inner end 51 and an outer end 53, the ribbon extending from the outer surface of the proximal end portion of its respective arm, around the distal end of the respective arm and to the inner surface of its respective arm,
  c) a central ribbon 55 having a distal end portion 57 connecting to the upper and lower ribbons at a junction 59 and a proximal end portion 61,
  d) a housing 63 adapted to maintain the arms in opposition and comprising a throughbore (not shown), wherein the proximal end portion of each arm is disposed in the throughbore and the distal end of each arm extends out of the throughbore,
  e) a feeder 67 disposed at least partially within the throughbore, wherein actuation of the feeder moves the junction distally.

When graft is loaded between the arms of the delivery device, it may be delivered to the patient by simply turning the knob component 69 of the feeder. Rotation of the knob turns the gears 71, which cause the inner ribbons to move distally in a conveyor belt-like manner. The graft loaded on to the conveyor belt likewise moves distally out of the delivery device and into the patient.

In use, the preparation device shown in FIG. 11 may be advantageously used to prepare the delivery device with the graft. First, the surgeon obtains the graft material and morselizes it in the mortar 73 and pestal 75 components of the mixing device 77 shown in FIG. 11. The graft is now ready to be loaded into the delivery device.

As a first step, the proximal end of central ribbon is pulled proximally so as to cause the upper and lower ribbons to move proximally as well. This "re-set" activity maximizes the amount of ribbon available for the graft.

Next, the surgeon places the lower arm of the delivery device within the groove 79 disposed along the front of the mixing device, and pivots the upper arm about a hinge 87 so as to reveal the inner surfaces of each arm to the surgeon. The surgeon then places the packed graft onto the ribboned lower arm, and then closes the upper arm upon the lower arm. The surgeon then removes the delivery device from the preparation device, so that the delivery device with the graft contained between its ribbons is now ready for use.

Next, the distal ends of the delivery device arms are placed within an intervertebral disc space. Actuation of the knob component of the delivery device has the effect of causing the inner portions of the ribbon to move distally while the arms remain in place. Because the graft lies on the ribbons, it moves distally in a conveyor belt-like manner across the inner surfaces of the arms and out of the delivery device and into the disc space.

In some embodiments, the delivery device further comprises f) a graft material 83 disposed between the upper and lower ribbons. This allows the invention to be used in the course of a spinal fusion procedure.

In some embodiments, the feeder comprises a proximal knob 69 and a distal cylinder 72 extending therefrom, the cylinder having a thread 73 thereon. This allows the surgeon the convenient ability to manually turn the knob and cause the graft to exit the delivery device.

In some embodiments, the feeder further comprises upper and lower gears 71 contacting the thread of the feeder and their respective ribbons. These gears represent a simple means for transferring manual energy from the knob into conveyor belt motion.

In some embodiments, the feeder has a throughbore (not shown), and the proximal end of the central ribbon extends through the throughbore. This embodiment allows the surgeon to "re-set" the conveyor belt to its proximal-most location, thereby maximizing the amount of graft that can be delivered.

In some embodiments, the upper and lower arms of the delivery device comprise a single tube. This ensures that no graft can escape from between the two arms.

Figure 12A:
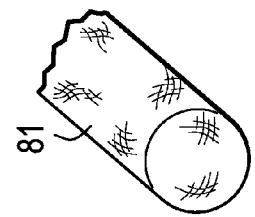
FIGS. 12A-C disclose different conveyor belts of the present invention.
Figure 12B:
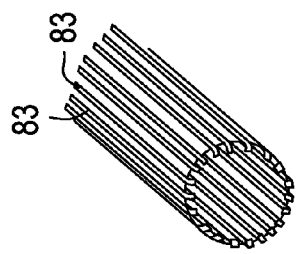
Figure 12C:
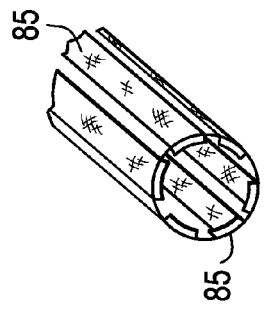

In some embodiments, and now referring to FIG. 12A, the upper and lower ribbons comprise a single sock 81. This ensures that no graft can escape from between the upper and lower ribbon. Likewise, the upper and lower ribbons can comprise a plurality of sutures 83 (FIG. 12B) or a plurality of ribbons 85 (FIG. 12C).

In some embodiments, the proximal end portion of each arm is pivotable and comprises a hinge 87. This allows the arms of the delivery device to be opened to the surgeon, thereby maximizing the amount of graft that can be placed within the delivery device.

In a second delivery device embodiment, and now referring to FIGS. 13A-F, there is provided a graft delivery system 103 comprising:
  a) a funnel 105 having a proximal frustoconical portion 107, a distal cylindrical portion 109 and a bore 111 defining an inner surface 113 and an outer surface 115,
  b) a plurality of ribbons 117, each ribbon extending in a continuous loop through the bore and around the outer surface of the funnel,
  c) a plurality of gears 119 disposed about a periphery of a proximal portion of the frustoconical portion, each gear having a toothed portion 121 and a cylindrical portion 123,
  d) a knob 125 disposed about a periphery of the gears, the knob having a threaded portion 127 that mates with the toothed portion of each gear so that rotation of the knob turns the gears,
wherein each ribbon contacts the toothed portion of its respective gear.

When graft is loaded between the arms of the delivery device, it may be delivered to the patient by simply turning the knob component. Rotation of the knob turns the gears, which cause the inner portion of each ribbon to move distally in a conveyor belt-like manner. Graft 129 housed in the reservoir 131 is thereby drawn onto the conveyor belt, moves along with the conveyor belt distally, and proceeds out of the delivery device and into the patient.

In use, the surgeon first obtains bone from the patient and places it in the reservoir 131 of FIG. 13B. The surgeon then puts together the assembly of FIG. 13A, whose proximal components are shown in FIG. 13B and include the reservoir 131, a bone mill 133, a bone mixer 135, a cover 137 and a power unit 139. When the power unit is actuated, the bone is morselized and mixed with other liquid components (such as biological and pharmaceutical additives) in preparation for loading onto the distal cylindrical portion.

Next, the distal cylindrical portion of the funnel is removed from the power unit and mounted to the proximal end of the delivery device, and the distal end of the delivery device is placed within an intervertebral disc space. Actuation of the knob component of the delivery device has the effect of turning the gears to thereby cause the inner portions of the ribbon to move distally in a conveyor belt-like manner while the funnel remains in place. Because the graft lies on the ribbons, it moves distally across the inner surface of the funnel, out of the delivery device and into the disc space.

In some embodiments, the system is loaded with bone graft material disposed within the bore of the funnel, so as to be useful in spinal fusions.

In some embodiments, the system further comprises a washer 141 having an inner surface 143 and disposed about a junction 145 of the distal cylindrical portion and the proximal frustoconical portion of the funnel, wherein the inner surface of the washer contacts each ribbon. This washer keeps the ribbons close to the outside surface of the funnel, thereby maximizing the streamline nature of the delivery device.

Figure 13C:
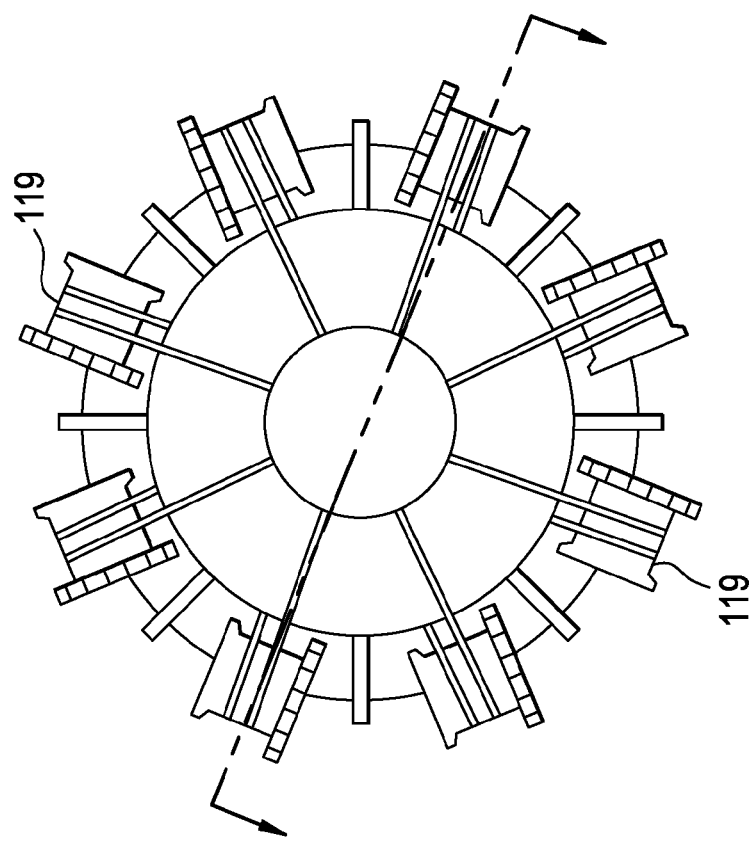
Figure 13D:
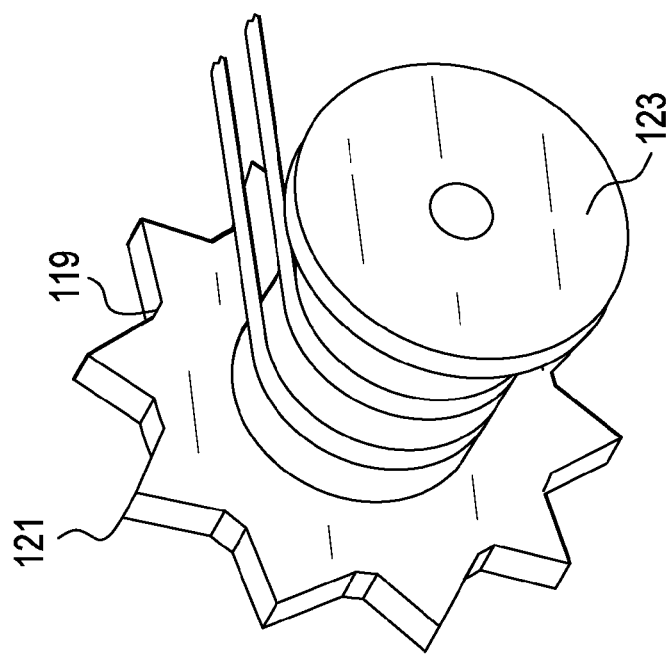

In some embodiments, as in FIG. 13D, at least one ribbon wraps completely around a cylindrical portion of a gear. This allows side-by-side portions of the same ribbon to extend to the inside of the tube and the outside of the tube.

In some embodiments, the system further comprises a reservoir 131 attached to the proximal end of the device (e.g., the knob or proximal frustoconical portion of the funnel). This reservoir holds the bone that has been milled in the FIG. 13B assembly in a manner that is convenient for its delivery into the conveyor belt.

In some embodiments, the assembly contains a bone mill that acts as a morselizer.

In some embodiments, the threaded portion of the knob mates with the toothed portion of each gear to create a worm gear. This is a convenient means for converting rotational energy into translational energy.

Figure 14A:
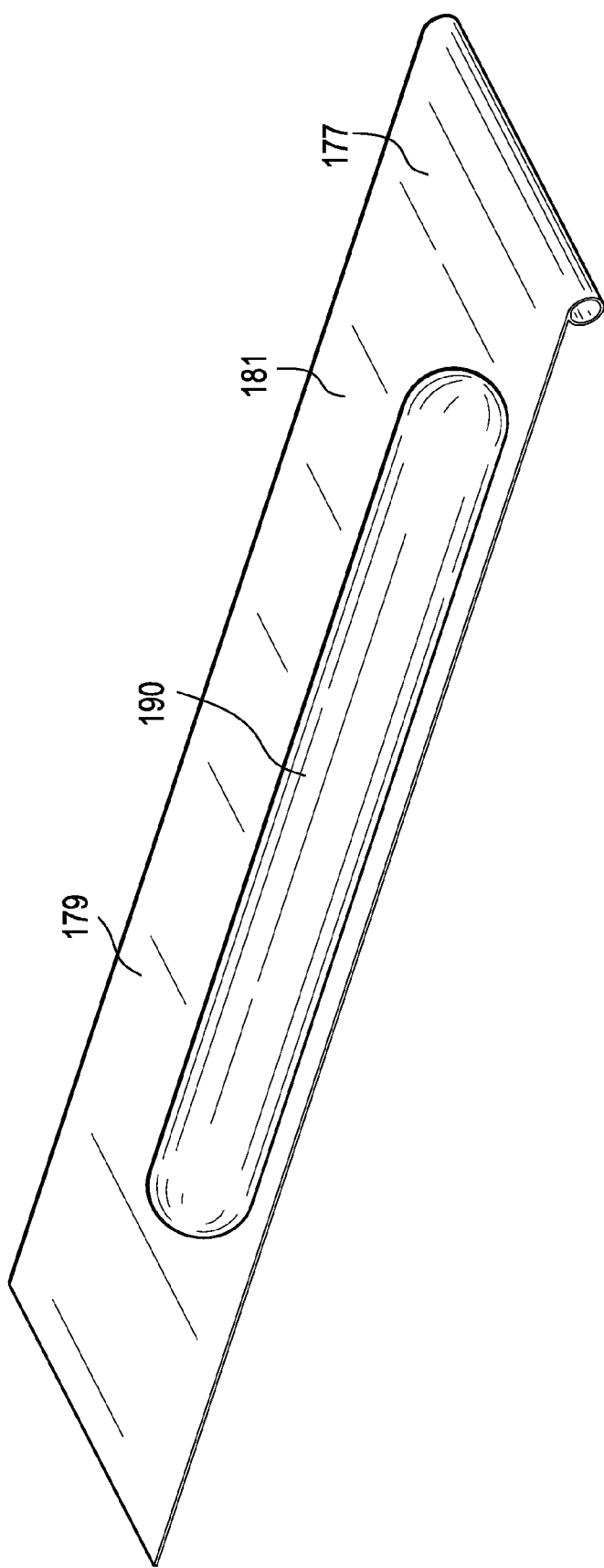
FIGS. 14A-14W disclose a third delivery device of the present invention.

In a third delivery device embodiment, and now referring to FIGS. 14A-14V, there is provided a graft delivery system 151 comprising:
- a) an inner tube 153 having an outer surface 155, an inner surface 157, a proximal end portion 159 and a distal end 161,
- b) an outer tube 163 having an outer surface 165, a proximal end portion 167 and a distal end portion 169,
- c) a lock ring 171 having a proximal end 173 and a distal end 175,
- d) a sheet 177 having a proximal end portion 179 and a distal end portion 181, the sheet forming a bore 183, wherein the outer surface of the inner tube is slidingly received in the inner surface of the outer tube, wherein the lock ring is coupled to the distal end portion of the outer tube, forming an interface therebetween, wherein the proximal end portion of the sheet is at least partially received within the inner tube, and wherein the distal end portion of the sheet at least partially extends out of the distal end of the inner tube and is disposed at the interface between the lock ring and the distal end portion of the outer tube.

Graft is first loaded onto the sheet, which is then made into a roll and inserted into the distal end of the inner tube bore. The distal end of the sheet is then secured to the outer tube by a lock ring. The graft may be delivered to the patient by simply moving the outer tube proximally. Such proximal movement causes similar proximal movement of the distal portion of the sheet roll, which causes an opposite distal movement of the proximal portion of the sheet roll in a conveyor belt-like manner. Graft moves along with the conveyor belt distally, and proceeds out of the delivery device and into the patient.

In some embodiments, system further comprises e) bone graft disposed within the bore of the sheet. The selection of bone graft allows the delivery device to be used in a spinal fusion procedures.

In some embodiments, the sheet is in the form of a roll. That is, the sheet is in the form of a tightly-wound spiral. This allows the surgeon to conveniently place the graft onto the opened sheet and thereafter manipulate the sheet to provide a tube.

In some embodiments, the sheet is in the form of an integral tube.

In some embodiments, the lock ring is a separate component from the outer tube, while in others the lock ring is integral with the outer tube.

In some embodiments (FIG. 14W), the system further comprises: f) a retention ring 185 attached to the distal end of the sheet, wherein the retention ring is disposed between the lock ring and the distal end portion of the outer tube. This retention ring guarantees that the sheet that is made into a tube remains in tubular form. The retention ring may be coupled to regularly-spaced pegs 187 extending from the distal end portion of the sheet.

In some embodiments, a distal end of the sheet is folded. This folded end allows for a better locking of the sheet between the lock ring and the outer tube.

In some embodiments, the proximal end portion of the outer tube further comprises a handle 188. This allows the outer tube to be conveniently grasped as it is pulled proximally.

Figure 14B:
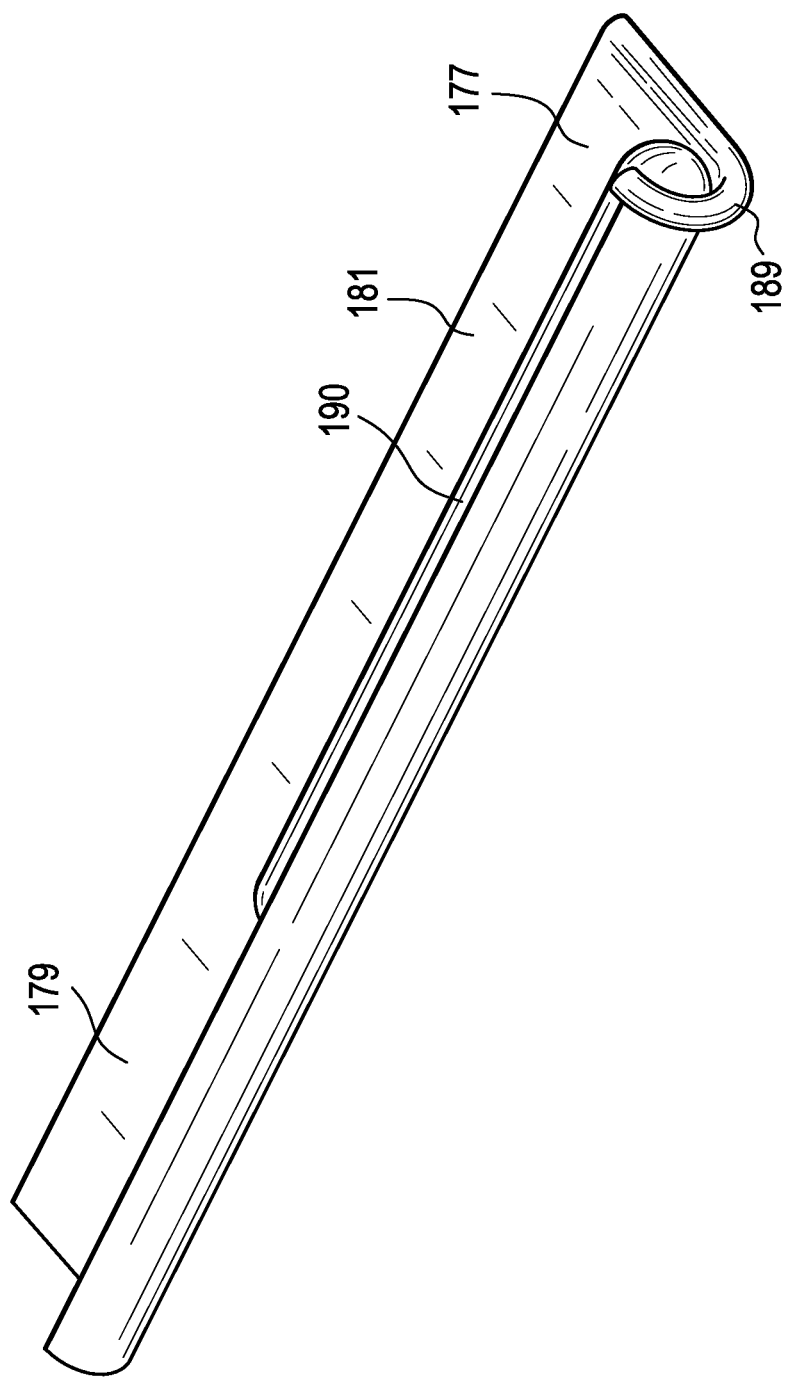

Now referring to FIG. 14A, the graft material 190 is packed and placed on the sheet. In FIG. 14B, the distal end of the sheet is folded to form a ring 189. In FIGS. 14B and C, the sheet is folded lengthwise around the graft to form a tube. In FIG. 14D, the sheet in tubular form is aligned with the bore of the inner tube in preparation of insertion of the sheet (and its contained graft) into the inner tube. In FIG. 14E1, the proximal end portion of the sheet is inserted into the bore of the inner tube. In FIG. 14E2, the tubular sheet (and its contained graft) is substantially fully inserted into the bore of the inner tube. FIG. 14F shows a side view of FIG. 14E2.

In FIG. 14G, the distal end of the sheet that was in the form of a ring is now partially unfolded to wrap around the distal end of the inner tube. FIG. 14H shows a cross-section of FIG. 14G.

FIG. 14I shows a cross-section in which the ring at the distal end of the sheet is further unfolded.

FIG. 14J shows the lock ring aligned with the distal end of the inner tube that now contains the sheet-graft assembly.

Figure 14K:
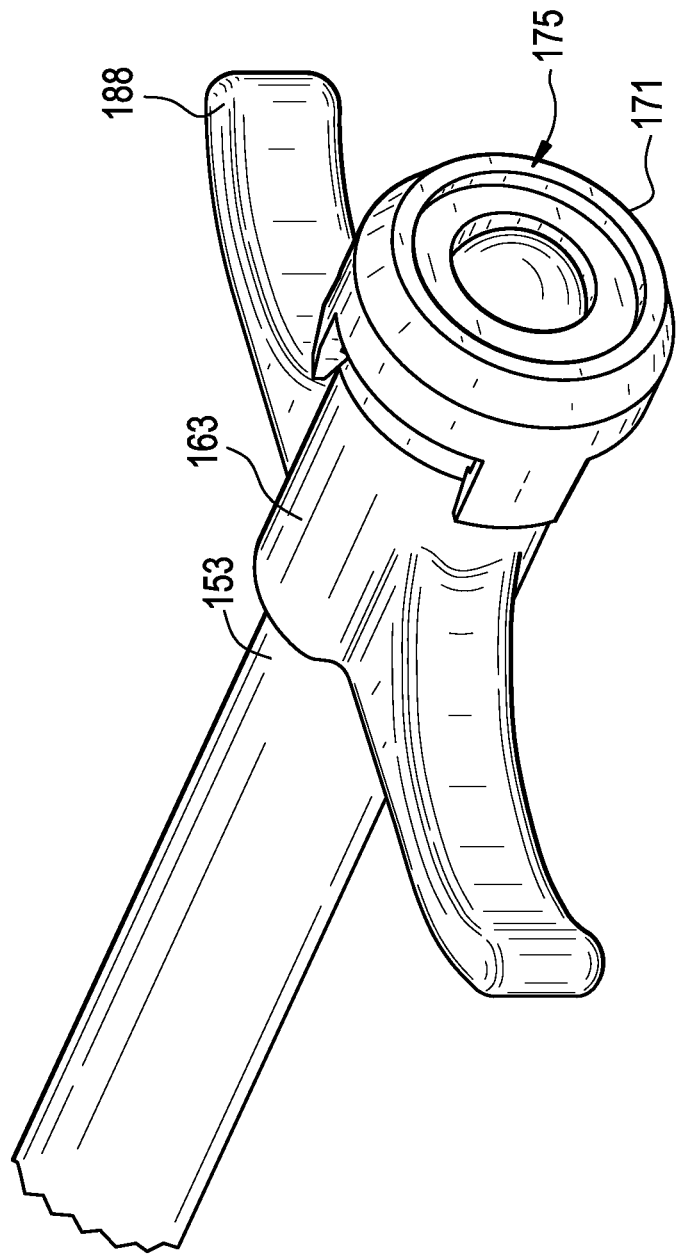
Figure 14L:
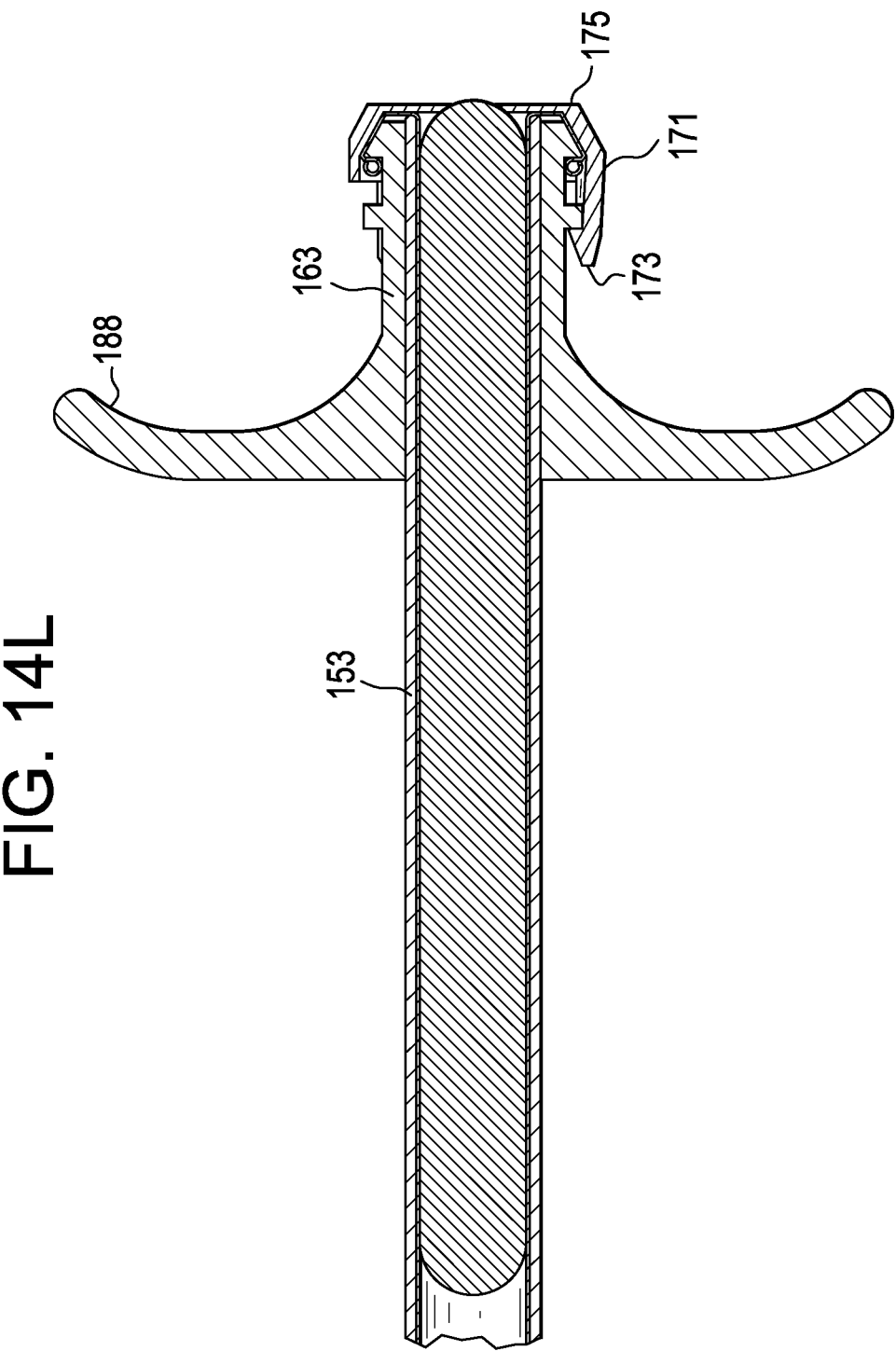

FIG. 14K shows the lock ring locked onto the distal end of the inner tube that now contains the sheet-graft assembly. FIG. 14L is a cross-section of FIG. 14K.

FIG. 14M shows how initial distal movement of the handled outer tube draws the sheet (and its attendant graft) out of the inner tube.

Figure 14N:
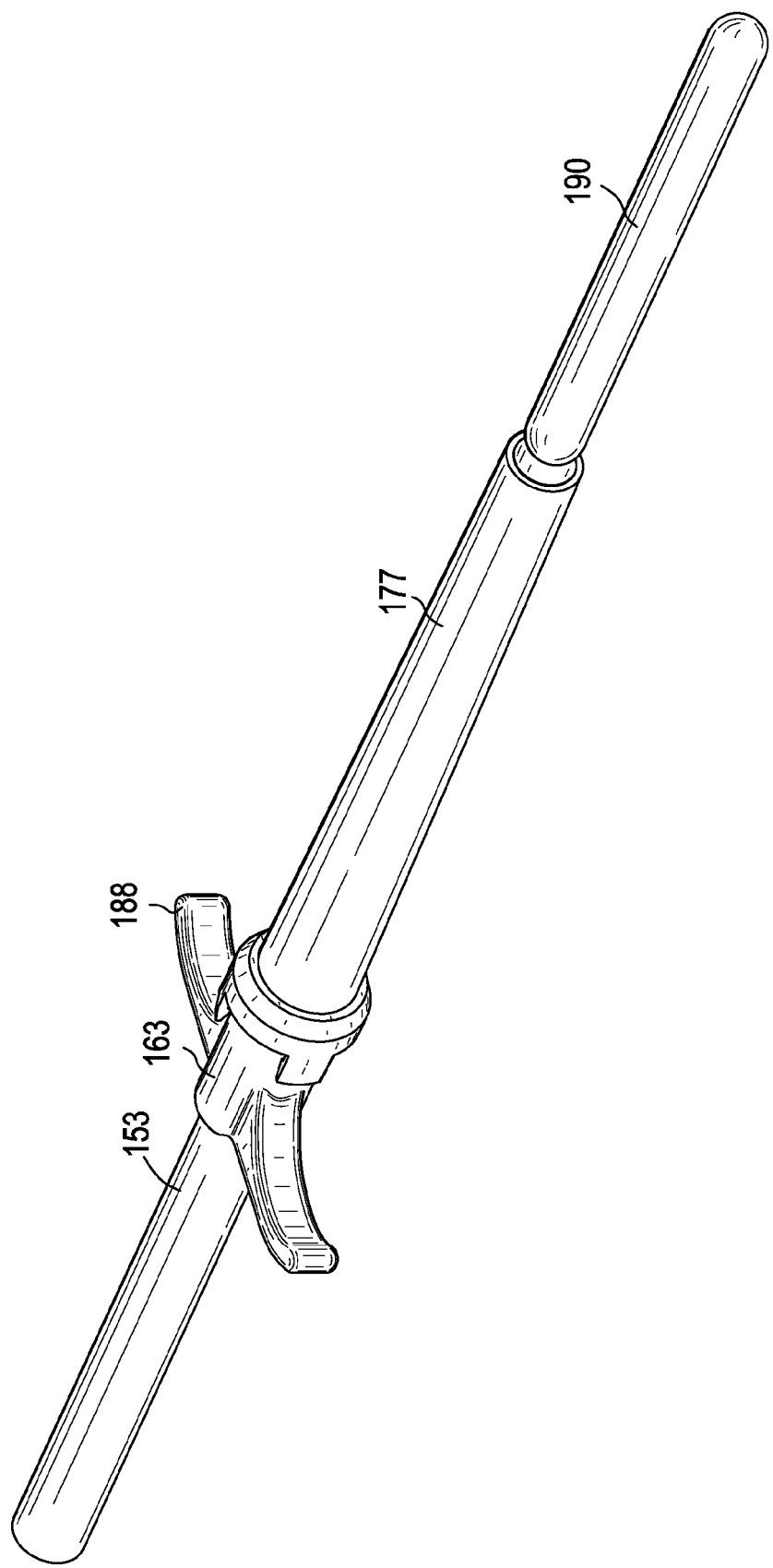
Figure 14P:
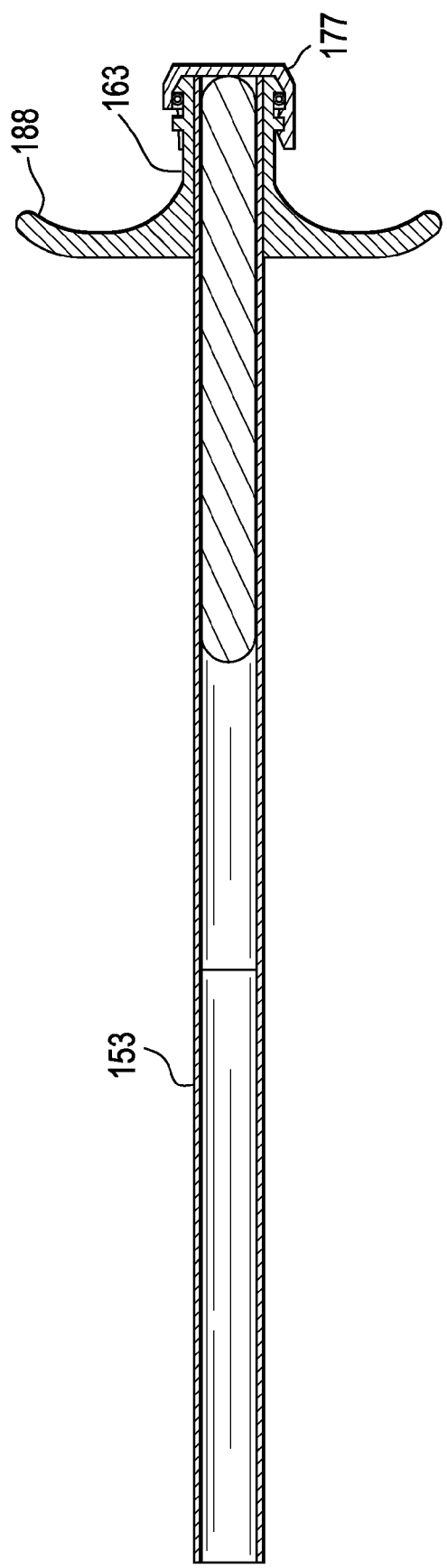
Figure 14R:
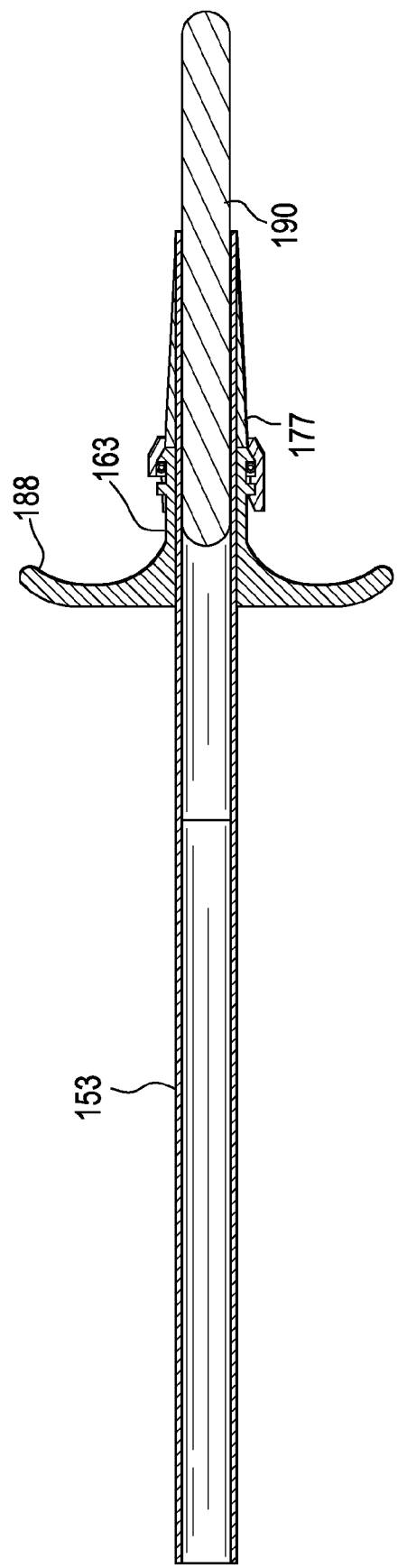
Figure 14T:
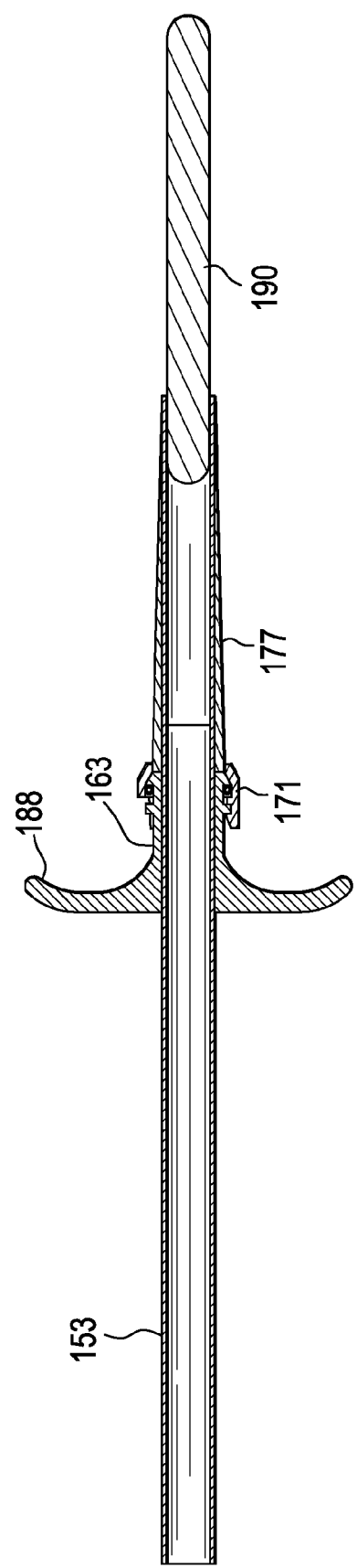
Figure 14U:
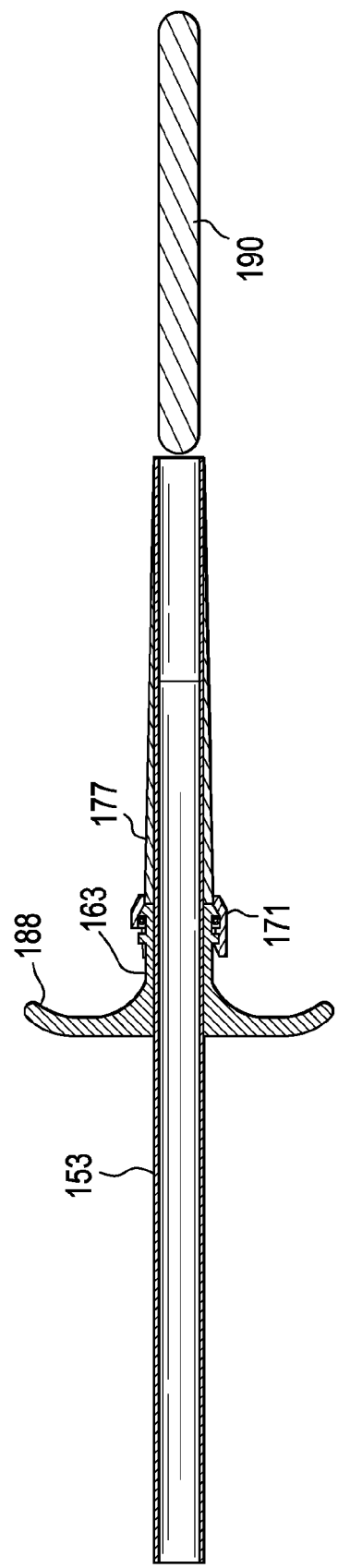
Figure 14W:
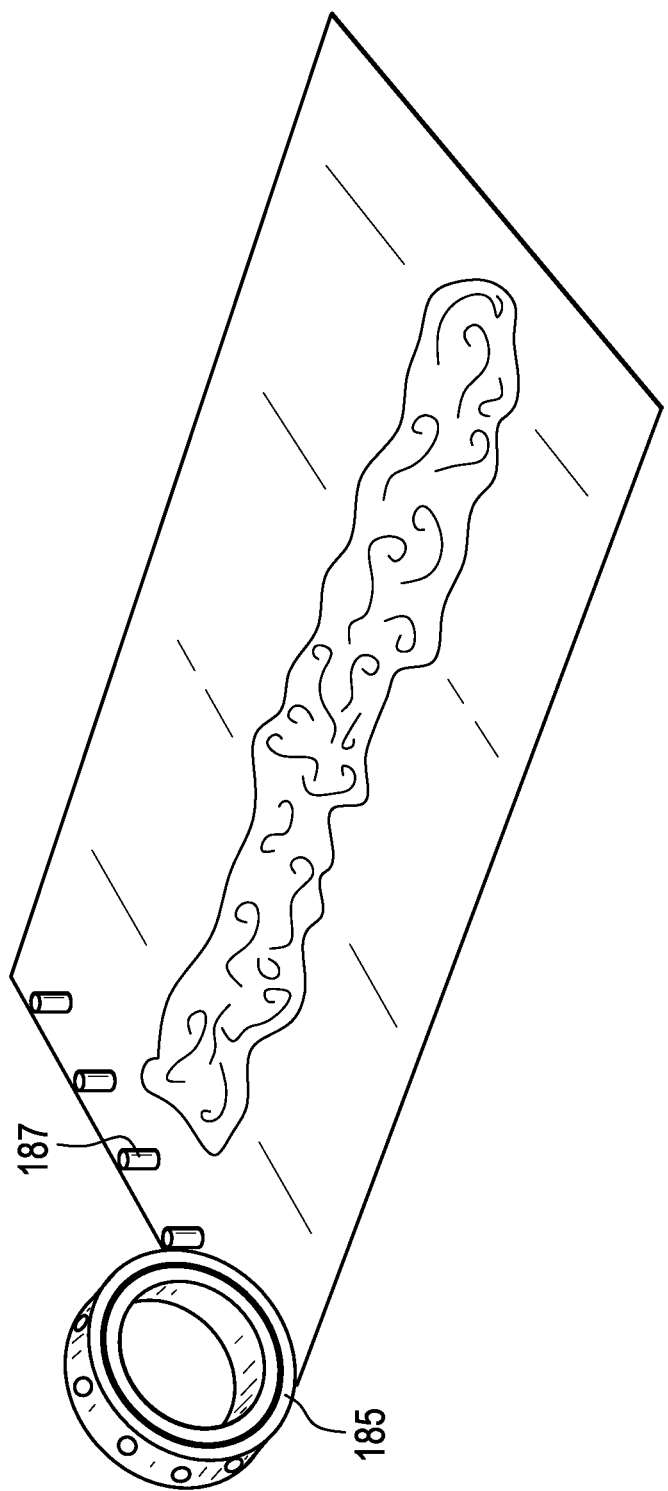

FIG. 14N shows how continued distal movement of the handled outer tube further draws the sheet (and its attendant graft) out of the inner tube.

FIGS. 14P-14U show sequential cross-sections in which distal movement of the handled outer tube further draws the sheet (and its attendant graft) out of the inner tube.

Figure 15:
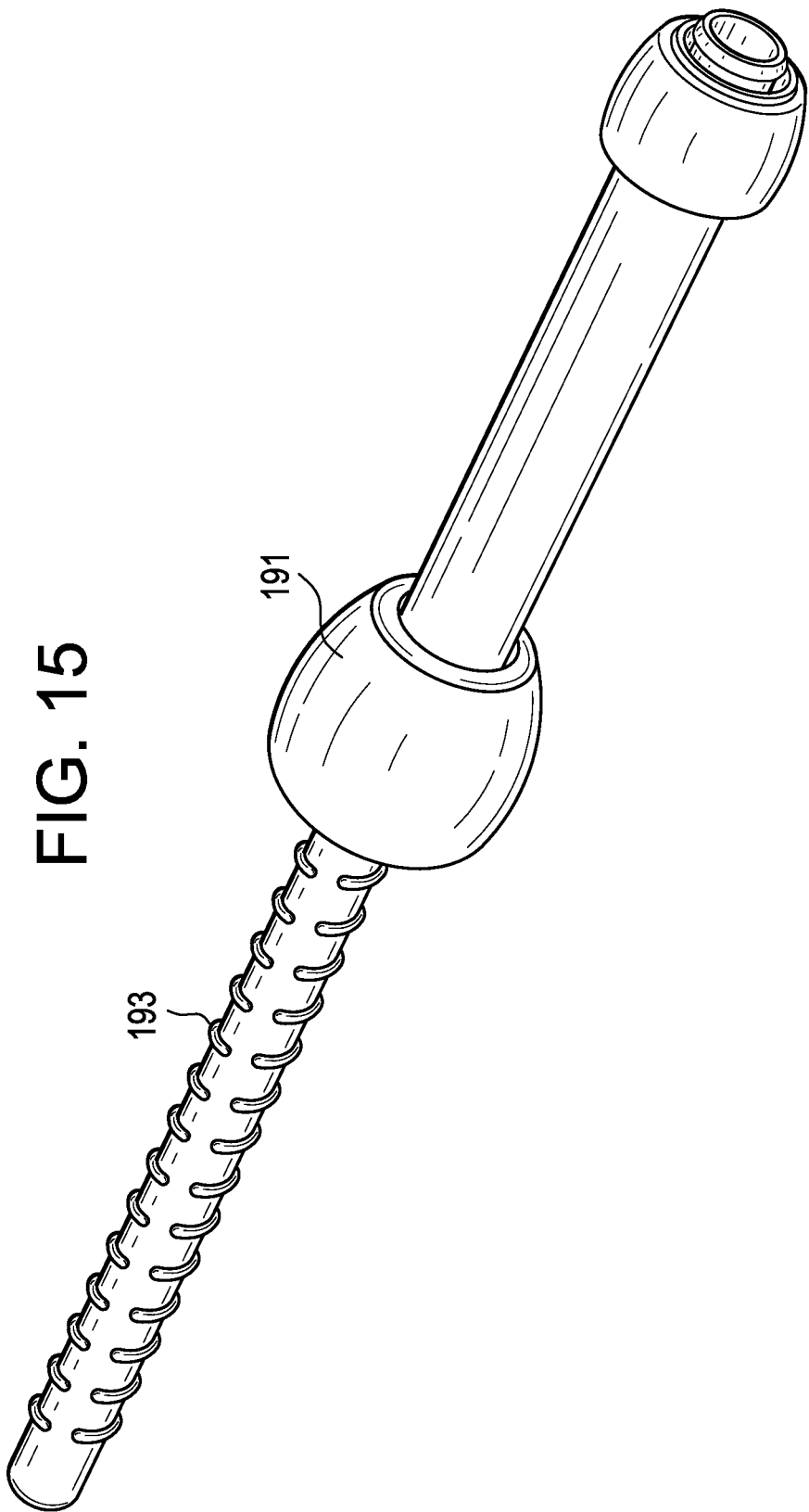
FIG. 15 discloses a fourth delivery device of the present invention.

FIG. 15 presents an alternate embodiment wherein the handle of the outer tube is replaced with a threaded knob 191 and the outer surface of the inner tube has a mating thread 193 thereon.

Therefore, generally, the broad scope of the present invention includes a method for delivering graft, comprising the steps of:
- a) providing a delivery device comprising:
  - i) upper and lower opposing arms, each arm having a proximal end portion and a distal end, an outer surface and an inner surface,
  - ii) upper and lower ribbons, each ribbon having an inner end and an outer end, the ribbon extending from the outer surface of the proximal end portion of its respective arm, around the distal end of the respective arm and to the inner surface of its respective arm,
  - iii) a graft material disposed between the upper and lower ribbons,
- b) inserting the distal end of each arm into a space in a patient,
- c) moving the inner ends of each ribbon distally to eject the graft from the delivery device.

Preferably, the space in the patient is an intervertebral disc space. Preferably, the graft material is bone graft material, so as to allow for a spinal fusion. Preferably, the upper and lower arms comprise a single tube so as to insure the graft does not escape the device. Also preferably, the upper and lower ribbons comprise a single sock so as to insure that the graft does not escape the conveyor belt.

Also generally, the broad scope of the present invention includes a delivery device for delivering graft, comprising:
  a) upper and lower opposing arms, each arm having a proximal end portion and a distal end, an outer surface and an inner surface,
  b) upper and lower ribbons, each ribbon having an inner end and an outer end, the ribbon extending from the outer surface of the proximal end portion of its respective arm, around the distal end of the respective arm and to the inner surface of its respective arm,
  c) a graft material disposed between the upper and lower ribbons.

Preferably, the upper and lower arms comprise a single tube, and the upper and lower ribbons comprise a single sock.

In addition to the use of this delivery device in the delivery of graft to an intervertebral disc space, it is further envisioned that the delivery device may be advantageously used in delivery of graft into the lateral gutter of the spine for the purposes of enhancing lateral mass fusion.

We claim:

1. A unitary intervertebral fusion cage comprising:
  a) a base having a proximal surface and a distal surface, and
  b) at least three elastically deformable fingers extending distally from the base in a plane,
wherein the cage has an upper surface characterized by a width W and a length L, and
wherein an area of the upper surface of the cage is more than 60% of the area represented by L×W.

2. The cage of claim 1 further comprising a throughhole beginning on a proximal surface of the base and opening on a distal surface of the base.

3. The cage of claim 2 wherein at least one finger comprises a substantially transverse throughhole.

4. The cage of claim 2 wherein each finger comprises a substantially transverse throughhole.

5. The cage of claim 1 wherein each finger has a tip, and wherein the cage
  further comprises a flexible container material that connects the finger tips of the cage.

6. The cage of claim 1 having extreme fingers forming an angle of at least 45 degrees.

7. The cage of claim 1 wherein the fingers comprise a porous material such that graft material injected into the cage can flow through the porosity of the fingers.

8. The cage of claim 1 wherein each finger has a tip, wherein the tips correspond substantially to a perimeter of a vertebral endplate.

9. The cage of claim 1 having a collapsed form and a expanded form, wherein the cage in its collapsed form has a length of at least 45 mm and a length-to-width ratio of at least 2.5:1.

10. The cage of claim 1 wherein each finger has a tip, wherein the expanded form has a longitudinal axis, and wherein the tips of the extreme fingers extend laterally from the longitudinal axis.

* * * * *